(12) United States Patent
Pessala et al.

(10) Patent No.: US 10,328,221 B2
(45) Date of Patent: Jun. 25, 2019

(54) ANESTHETIC BREATHING APPARATUS WITH TARGET VALUE CONTROL OF ANESTHETIC AGENT

(71) Applicant: Maquet Critical Care AB, Solna (SE)

(72) Inventors: Tom Pessala, Bromma (SE); Mari Andersson, Stockholm (SE); Bengt Johansson, Bromma (SE); Stig Andersson, Spanga (SE); Mattias Rodehed, Sundbyberg (SE)

(73) Assignee: Maquet Critical Care AB, Solna (SE)

( * ) Notice: Subject to any disclaimer, the term of this patent is extended or adjusted under 35 U.S.C. 154(b) by 1045 days.

(21) Appl. No.: 14/291,333

(22) Filed: May 30, 2014

(65) Prior Publication Data
US 2014/0352693 A1 Dec. 4, 2014

(30) Foreign Application Priority Data
May 31, 2013 (EP) ..................................... 13169950

(51) Int. Cl.
*A61M 16/00* (2006.01)
*A61M 16/08* (2006.01)
(Continued)

(52) U.S. Cl.
CPC ........ *A61M 16/0051* (2013.01); *A61M 16/01* (2013.01); *A61M 16/026* (2017.08);
(Continued)

(58) Field of Classification Search
CPC ............ A61M 16/009; A61M 16/0093; A61M 16/01; A61M 16/0891; A61M 2016/102;
(Continued)

(56) References Cited

U.S. PATENT DOCUMENTS 7,229,430 B2  1/2007 Hickle et al.
7,997,268 B1  8/2011 Leonard et al.
(Continued)

FOREIGN PATENT DOCUMENTS

EP   1 961 438   8/2008
EP   1 961 439   8/2008
(Continued)

OTHER PUBLICATIONS

Chinese Office Action Including Search Report dated Mar. 1, 2017.

*Primary Examiner* — Michael J Tsai
(74) *Attorney, Agent, or Firm* — Fay Kaplun & Marcin, LLP

(57) ABSTRACT

An anesthetic breathing apparatus has a processing unit, a breathing circuit for providing an inspiratory patient gas mixture of re-breathed gas and/or fresh gas to a patient fluidly connected to the breathing circuit, and a fresh gas supply controllable by the processing unit for supplying a flow of the fresh gas to the breathing circuit in a composition including oxygen and at least one anesthetic agent (AA). A user interface includes a first user input element for receiving operator input for an anesthetic target value including an end expiratory concentration of the AA (EtAA) target value and/or an end expiratory minimum alveolar concentration (EtMAC) target value of an end expiratory MAC value of the patient, and a second user input element for receiving operator input for a desired control profile for the fresh gas supply for obtaining at least the anesthetic target value. The inspiratory patient gas mixture is controlled based on at least the anesthetic target value, the oxygen target value, and the desired control profile.

12 Claims, 11 Drawing Sheets

(51) Int. Cl.
*A61M 16/12* (2006.01)
*A61M 16/10* (2006.01)
*A61M 16/01* (2006.01)
*A61M 16/18* (2006.01)

(52) U.S. Cl.
CPC ...... *A61M 16/0891* (2014.02); *A61M 16/104* (2013.01); *A61M 16/1015* (2014.02); *A61M 16/122* (2014.02); *A61M 16/18* (2013.01); *A61M 2016/1025* (2013.01); *A61M 2016/1035* (2013.01); *A61M 2205/505* (2013.01); *A61M 2205/581* (2013.01)

(58) Field of Classification Search
CPC ........ A61M 2016/1035; A61M 16/104; A61M 2230/437
See application file for complete search history.

(56) References Cited

U.S. PATENT DOCUMENTS

| | | | |
|---|---|---|---|
| 8,038,642 | B2 | 10/2011 | Tolvanen-Laakso et al. |
| 2007/0089741 | A1* | 4/2007 | Bohm ................. A61M 16/01 128/203.12 |
| 2008/0011294 | A1 | 1/2008 | Heesch et al. |
| 2011/0094509 | A1 | 4/2011 | Heinonen et al. |
| 2011/0168177 | A1 | 7/2011 | Connor |

FOREIGN PATENT DOCUMENTS

| | | |
|---|---|---|
| EP | 2 085 107 | 8/2009 |
| EP | 2 316 515 | 5/2011 |
| EP | 2 572 748 | 3/2013 |
| JP | 2003164526 | 10/2003 |

* cited by examiner ly, it should be understood that these state-
ANESTHETIC BREATHING APPARATUS WITH TARGET VALUE CONTROL OF ANESTHETIC AGENT

BACKGROUND OF THE INVENTION

Field of the Invention

This invention pertains in general to the field of inhalational anesthesia. More particularly the invention relates to an anesthetic breathing apparatus, and more particularly to a control process in such apparatus for obtaining specific target values of patient breathing gases.

Description of the Prior Art

This section is intended to introduce the reader to various aspects of art that may be related to various aspects of the present disclosure, which are described and/or claimed below. This discussion is believed to be helpful in providing the reader with background information to facilitate a better understanding of the various aspects of the present disclosure. Accordingments are to be read in this light, and not as admissions of prior art.

Operators of anesthetic breathing apparatuses previously have spent valuable time adjusting and checking anesthetic breathing parameters, like foremost inspired oxygen and anesthetic agent values, constantly re-adjusting these parameter settings due to changes in uptake and metabolic rate of the anesthetized patient, to ensure safe and effective anesthesia. All this was done by the clinical operator of the apparatus in parallel with a multitude of other time-consuming and complex tasks. Recently anesthetic breathing apparatus are disclosed in which the operator is able to set the target values for these anesthetic breathing parameters and the apparatus automatically adjusts gas delivery to achieve and maintain the set target values. For instance, in United States patent application number US 2009/0050148, an inhalation anesthesia delivery system is disclosed, whereby the system comprises a fresh gas feeding arrangement connected to a breathing circuit, a monitor device, a control device and an interface unit. The fresh gas feeding arrangement and the ventilator are configured to deliver a desired concentration of gas to the breathing circuit, the desired concentration being set by using the interface unit. The monitor device is configured to monitor gas concentrations in the breathing circuit by analyzing gases flowing in the breathing circuit, and the control device is configured to control the fresh gas feeding arrangement on the basis of the data received from the monitor device to keep the desired breathing gas concentration. The monitor device is configured to monitor expired inorganic gas concentration by comparing the measured expired breathing gas concentration with the set target value and changing the fresh gas delivery accordingly to meet the target value.

However, the system disclosed in US 2009/0050148 has limitations, in particular when changing set target values. For instance during induction when ramping up concentration of an anesthetic agent (AA) to a clinically desired target value, the change may be provided in a non-desired way for certain patients. For instance, some brittle patients might be hit by sudden blood pressure drop or other side effects if delivered AA concentration is changed too quickly.

Therefore, inventors have identified the need for an anesthetic breathing apparatus in which the user may choose a desired control path from a current value of at least an AA concentration to a target value of the AA concentration. In this manner, the anesthetic breathing apparatus may be adjusted to obtain a certain AA target value in a clinically advantageous manner. In this manner for instance induction phases, emergence phase, or changes from one AA to another AA or a mixture thereof may be advantageously provided when using automatic control to reach desired clinical target values.

Hence, an improved anesthetic breathing apparatus would be advantageous and in particular allowing for increased flexibility, cost-effectiveness, and/or patient safety would be advantageous.

It is desired that patient safety be improved. An apparatus is desired in which some patients might be anesthetized slower than others, while other, less brittle patients might be anesthetized quicker, in particular in automatic anesthesia modes of the apparatus. Side effects when changing AA values delivered to a patient, like blood pressure drops, are desired to be avoided by such an improved apparatus. Also, during acute situations, like acute caesarian sections, anesthesia is desired to be provided as quickly as possible by such apparatus Economy of operating an anesthetic breathing apparatus is desired to be improved by such improved apparatus. For instance, a slower ramping up to a desired AA level might be economically more advantageous as expired AA might be more efficiently re-breathed. Wash out of AA and wake-up is desired to be more effectively controlled and predicted. Patient throughput in OR theatres might be increased if for instance predicted times for AA target changes to be effected are provided by the apparatus in a reliable manner. Hence, some improved anesthetic breathing apparatus are desired to provide such estimated times until a set anesthetic target is obtained.

SUMMARY OF THE INVENTION

Accordingly, examples of the present invention preferably seek to mitigate, alleviate or eliminate one or more deficiencies, disadvantages or issues in the art, such as the above-identified, singly or in any combination by providing an apparatus, control processes, methods and a computer program according to the appended patent claims.

In an aspect of the disclosure, an anesthetic breathing apparatus or control process is provided, in which the operator of the apparatus can select a desired control path from a current value of at least an AA concentration to a target value of the AA concentration. The apparatus then automatically sees to that such anesthetic target value is obtained via the control path chosen by the operator. The selection of the control path by the operator may include selecting a specific rate of change from a range of such rates. In this manner, the anesthetic breathing apparatus is operator adjustable to obtain a certain anesthetic target value, such as an AA concentration target value or a MAC target value explained below, in a clinically advantageous manner. In this manner for instance induction phases, emergence phase, or changes from one AA to another AA or a mixture thereof may be advantageously provided when using automatic control to reach desired clinical anesthetic target values. The control path may be based on controlling a mixture of fresh gas and re-breathed gas at a profile that corresponds to the control path. The control path is advantageously including a feedback loop from measured values, such as including end expiratory concentration of an AA value, namely an anesthetic target value for the end tidal anesthetic agent concentration (EtAA), or an inspiratory oxygen portion in the inspiratory patient gas (FiO2). An estimated duration until one or more anesthetic target values are reached may be calculated. The duration can be provided to the operator as a predicted value before and during application of the selected control path. The operator may thus take an advantageous clinical decision in dependence of the estimated duration to reach the one or more anesthetic target values.

Patient safety may thus be improved. Some patients might be anesthetized to a desired depth of anesthesia slower than others, while other, e.g. less brittle patients might be anesthetized quicker. Also, during acute situations, like acute caesarian sections, anesthesia might be provided as quickly as possible. Side effects like blood pressure drops might be avoided.

Economy of operating an anesthetic breathing apparatus might be improved. For instance, a slower ramping up to a desired AA level might be economically more advantageous as expired AA might be more efficiently re-breathed. Wash out of AA and wake-up may be more effectively controlled and predicted. Patient throughput in OR theatres might me increased if for instance predicted times for AA target changes to be effected are provided by the apparatus in a reliable manner.

A visualization of an estimated duration and/or a graph illustrating a path of a control parameter, such as EtAA or FiO2, until a target is reached is in an example displayed. Such display is only done during an activated automatic gas control operational mode of the apparatus. Such visualization provides the operator with a direct feedback of the consequences of selecting a certain control path, such as a SPEED parameter explained below. The operator may select a certain control path, whereupon the estimation is updated and displayed. The selected control path may then be implemented for continued operation of the apparatus, either with or without a separate confirmation input.

Once the selected control path is implemented, the estimation is in examples continuously updated. In case a change of parameters occurs, which influence the estimation, e.g. a change of patient uptake of AA, the estimation is updated and duration and/or the estimated graph to reach the target is updated.

The graph may include a trend part for past values of the control parameter which target is to be obtained. The trend allows the operator to better understand the estimated continued path towards reaching the target, i.e. to understand the context of the development of the control parameter towards the selected anesthetic target value.

When one or more target values are reached, such as an anesthetic target value for an EtAA concentration, the operator may be provided with information that the target is reached. A sound may be provided informing the operator of the reached target(s). It might be of clinical importance for the operator to be timely informed of the target being reached, which otherwise might be missed by the operator when having attention directed away from the graphical display.

AA in the present context pertains to gaseous or gasifiable substances that produce anesthesia by inhalation. AA include substances commonly known as volatile anesthetic agents, including ethers and haloalkanes, such as Desflurane, Enflurane, Isoflurane, Halothane or Sevoflurane. The term AA also includes other gases or vapors that produce or maintain some level of anesthesia, such as Nitrous Oxide (N2O), Cyxlopropane, Xenon, also including adjunct anesthetics used along with other AAs.

The term "fresh gas" in the present application includes any volume of AA freshly vaporized in the fresh gas flow to the breathing circuit, besides O2(+Air or N2O).

According to an aspect of the disclosure, an anesthetic breathing apparatus is provided including a processing unit, a breathing circuit for providing an inspiratory patient gas mixture of re-breathed gas and/or fresh gas to a patient fluidly connected to the breathing circuit, and a fresh gas supply controllable by the processing unit for supplying a flow of the fresh gas to the breathing circuit in a composition including oxygen and at least one anesthetic agent (AA); wherein the apparatus has a user interface. The user interface includes a first user input element for receiving operator input for an anesthetic target value such as an end expiratory concentration of the AA (EtAA) target value. Alternatively on in addition, the anesthetic target value may include an end expiratory minimum alveolar concentration (MAC) target value of an end expiratory MAC value of the patient.

The operator can also choose an oxygen target value for an inspiratory oxygen portion in the inspiratory patient gas (FiO2), which inspiratory oxygen portion usually is implemented without substantial control delay in operation of the apparatus. A measured FiO2 is provided, usually by an oxygen measuring unit, such as of a multigas monitor measuring at a Y-piece.

The user interface includes also a second user input element for receiving operator input for a desired control profile for the fresh gas supply for obtaining at least the anesthetic target value. The processing unit is configured to control the inspiratory patient gas mixture based on at least the anesthetic target value and the desired control profile. The oxygen target value and/or the measured FiO2 value is taken into consideration for providing a desired inspiratory patient gas mixture. The oxygen target value or measured FiO2 value may be taken into consideration by the control process towards the target AA value. The oxygen target value rules for instance the remaining amount available for AA in the patient gas mixture, like N2O if used.

MAC is an abbreviation for "Minimum Alveolar Concentration" of anesthetic agents at a pressure of 1 atmosphere that produces immobility in 50 percent of those patient or animals exposed to a noxious stimulus. The MAC value is related to individual anatomical and/or physiological conditions, and is e.g. dependent on the age of the patient. The anesthetic agents mentioned above have in an example been found for a patient of 40 years of age: Halothane 0.8%, Enflurane 1.7%, Isoflurane 1.2%, Sevoflurane 2.1%, Desflurane 6.6%. Other AAs, like gaseous components, such as Nitrous Oxide (N2O), Xenon, etc. also have a MAC.

In an example, the processing unit is configured to control at least the fresh gas flow and composition for the control of the inspiratory patient gas mixture. In this manner the inspiratory patient gas mixture includes at least in a portion the fresh gas when supplied to the breathing circuit.

In an example, the control profile includes a desired rate of change for obtaining at least one of the target values.

In an example, the control profile includes a rate of change for obtaining the anesthetic target value from a current level of the EtAA.

In an example, the rate of change is selectable from a range for the rate of change having a minimum value and a maximum value, wherein the second user input element in particular includes a plurality of operator selectable discrete steps ranging from the minimum value to the maximum value.

In an example, the processing unit for the maximum value is configured to control the fresh gas flow to be the only gas composition in the inspiratory patient gas mixture delivered to the patient without re-breathed gas, and wherein the processing unit for values in the range of the rate of change other than the maximum value is configured to control the fresh gas flow to be less than a flow of the inspiratory patient gas mixture delivered to the patient with a re-breathed gas.

In an example, the processing unit is configured to provide a ramp function with a pre-defined pitch for each of the discrete steps between the current level of the EtAA and the anesthetic target value.

In an example, the processing unit is configured to calculate a time estimate until at least one of the target values is reached, wherein the processing unit is preferably configured to update the time estimate continuously until the at least one target value is reached.

In an example, the time estimate is updated based on measured EtAA values when the inspiratory patient gas mixture is being controlled by the processing unit based on at least the anesthetic target value and the desired control profile. The oxygen target value or measured FiO2 value may be taken into consideration by the control process.

In further examples, the anesthetic target is higher than a current EtAA value or higher than a current MAC value, such as during anesthesia induction, or the anesthetic target is lower than a current EtAA value or lower than a current MAC value, such as the anesthetic target value being zero for instance during anesthesia emergence for patient wake-up.

In an example, the at least one anesthetic agent (AA) includes at least a first AA and a second AA, and wherein the anesthetic target is based on the second AA when switching from the for first AA to the second AA, or the anesthetic target value is a mixed MAC target value for the first and second AA.

Mixed MAC refers to the cumulative MAC of several AA. The term mixed MAC sometimes also is referred to as total MAC. When having a mixture of several AAs, a mixed MAC may be calculated as a simple addition of the two MAC values of each of the anesthetic agents present in the mixture. In addition, a weighing of MAC efficiency parameters may contribute to the mixed MAC value, such as the type of anesthetic agent, patient related parameters, such as age, etc. This is in detail explained in international patent publication number WO2009/062540 of the same applicant as the present disclosure, which is incorporated herein by reference for all purposes.

In an example, the user interface includes a display unit operatively connected to the processing unit, and wherein the processing unit is configured to calculate an estimated duration or end time from a current time when at least one of the targets is reached and to preferably calculate an estimated path to reach the at least one target. The processing unit is further configured to communicate the duration or end time to the display for visualization, such as in a trend, which trend preferably including values of the EtAA and/or FiO2 measured before the current time, and the visualization including a preview of the estimated path from the current time at least during the duration or until the end time.

In an example, the processing unit is configured to continuously calculate and update the estimated duration or end time and/or the estimated path to reach the at least one target, based on measured values of the EtAA and/or FiO2.

According to yet another aspect of the disclosure, an anesthetic breathing apparatus is provided that includes a touch sensitive display unit and a processing unit being operatively connected to the display unit, a breathing circuit for providing an inspiratory patient gas mixture of re-breathed gas and/or fresh gas to a patient fluidly connected to the breathing circuit, and a fresh gas supply controllable by the processing unit for supplying a flow of the fresh gas to the breathing circuit in a composition including oxygen and at least one anesthetic agent (AA), the processing unit being configured to provide on the display unit a graphical user interface including a graphical visualization.

The graphical visualization includes a first user input element for receiving operator input on the touch sensitive display unit for an anesthetic target value including an end expiratory concentration of the AA (EtAA) target value and/or an end expiratory minimum alveolar concentration (MAC) target value of an end expiratory MAC value of the patient. The oxygen target value for an inspiratory oxygen portion in the inspiratory patient gas (FiO2) or currently measured FiO2 value may be taken into consideration by the control process. The graphical visualization includes also a second user input element for receiving operator input on the touch sensitive display unit for a desired control profile for the fresh gas supply for obtaining at least the anesthetic target value. Moreover, the graphical visualization includes a current time and an estimated duration or end time when at least one of the targets is reached and preferably an estimated path to reach the at least one target such as in a trend preferably including visualization of values of the EtAA and/or FiO2 measured before the current time and including a preview of the estimated path from the current time during the duration or until the end time.

According to a further aspect of the disclosure, an internal control process in an anesthetic breathing apparatus is provided for controlling delivery of an inspiratory patient gas mixture from a breathing circuit of the apparatus to a patient fluidly connected to the breathing circuit. The controlling of the inspiratory patient gas mixture includes providing a gas composition and gas flow of a fresh gas to the breathing circuit based on at least an anesthetic target value and a desired control profile, by controlling a fresh gas supply supplying the gas flow of the fresh gas to the breathing circuit in a composition including oxygen and at least one anesthetic agent (AA). The oxygen target value or measured FiO2 value may be taken into consideration by the control process. The controlling further includes providing the inspiratory patient gas mixture of re-breathed gas and/or the fresh gas in the breathing circuit to the patient. The anesthetic target value is provided by operator input of an end expiratory concentration of the AA (EtAA) target value and/or an expiratory Minimum Alveolar Concentration (MAC) target value of an end expiratory MAC value of the patient and the desired control profile for the fresh gas supply is operator input for obtaining at least the anesthetic target value. The oxygen target value or measured FiO2 value may be taken into consideration by the control process.

According to a further aspect of the disclosure, a computer-readable medium is provided having embodied thereon a computer program for processing by a processing unit of an anesthetic breathing apparatus for controlling delivery of an inspiratory patient gas mixture from a breathing circuit of the apparatus. The apparatus includes a touch sensitive display unit, and the processing unit is operatively connected to the display unit. The processing unit is further configured to provide on the display unit a graphical visualization. The computer program comprises code segments for providing the graphical visualization including code segments for providing a first user input element for receiving operator input on the touch sensitive display unit for an anesthetic target value including an end expiratory concentration of the AA (EtAA) target value and/or an end expiratory minimum alveolar concentration (MAC) target value of an end expiratory MAC value of the patient. The oxygen target value or measured FiO2 value may be taken into consideration by the processing unit. The computer program comprises code segments for providing a second user input element for receiving operator input on the touch sensitive display unit for a desired control profile for the fresh gas supply for obtaining at least the anesthetic target value. The computer program comprises code segments for providing a current time and an estimated duration or end time when at least one of the targets is reached and preferably an estimated path to reach the at least one target such as in a trend preferably including visualization of values of the EtAA and/or FiO2 measured before the current time and including a preview of the estimated path from the current time during the duration or until the end time.

According to another aspect of the disclosure, a method is provided for controlling delivery of an inspiratory patient gas mixture of re-breathed and/or fresh gas from a breathing circuit of an anesthetic breathing apparatus to a patient fluidly connected to the breathing circuit. The method includes receiving operator input for an anesthetic target value including an end expiratory concentration of the AA (EtAA) and/or an expiratory Minimum Alveolar Concentration (MAC) target value of an end expiratory MAC value of the patient. The oxygen target value or measured FiO2 value may be taken into consideration some examples of the method. The method includes further receiving operator input for a desired control profile for the fresh gas supply for obtaining the anesthetic target value. Moreover, the method includes providing the inspiratory patient gas mixture including a gas composition and gas flow of the fresh gas, by at least controlling a fresh gas supply for supplying the gas flow of the fresh gas to the breathing circuit in a composition including oxygen and at least one anesthetic agent (AA), the controlling being based on at least the anesthetic target value and the desired control profile for obtaining at least the anesthetic target value. The oxygen target value or measured FiO2 value may be taken into consideration when selecting an oxygen concentration value for the fresh gas composition by the processing unit and desired operator input.

According to yet another aspect of the disclosure, an anesthetic breathing apparatus is provided including a display unit and a processing unit being operatively connected to the display unit. The apparatus includes a breathing circuit for providing an inspiratory patient gas mixture of re-breathed gas and/or fresh gas to a patient fluidly connected to the breathing circuit. Further, the apparatus includes a fresh gas supply controllable by the processing unit for supplying a flow of the fresh gas to the breathing circuit in a composition including at least oxygen and air or nitrous oxide, and at least one anesthetic agent (AA). The apparatus has an automatic operational mode for delivery of inhalational anesthesia to the patient. The processing unit is configured to provide on the display unit a graphical user interface (GUI), during the automatic operational mode a graphical visualization. The GUI includes in combination a first visualization unit including a bar and metric for flow of a measured oxygen portion in the composition of the fresh gas flow, a bar and metric for flow of a measured nitrous oxide portion in the composition of the fresh gas flow or a bar and metric for flow of a measured air portion in the composition of the fresh gas flow, a bar and metric for flow of a measured portion of the AA in the composition of the fresh gas flow; and a second visualization unit including a metric for the total measured fresh gas flow updated for each breath supplied to the patient, and an animation for visualizing a fresh gas flow to the breathing circuit, the animation moving during ongoing fresh gas delivery to the breathing circuit only.

Further examples of the disclosure are defined in the dependent claims, wherein features for the second and subsequent aspects of the disclosure are as for the first aspect mutatis mutandis.

Advantages of the control process including a selectable control path, as described herein include amongst others:
an effective control of the rate of change is provided to obtain a desired anesthetic target value. A rate of change is selectable, allowing for a reliable prediction of a time to achieve the selected anesthetic target value.
a predictable mode is provided for controlling EtAA and its change over time
a control process for EtAA is provided that is independent of ventilatory settings and selected ventilatory parameters, such as Tidal Volume, Respiratory Rate, etc.
a control process is provided for EtAA that makes it possible to save costly anesthetic agents (except for the fastest control profile setting, which has other advantages though)
a control process is provided that assures for the fastest possible change of concentration of anesthetic agent and gas supply to a patient.

DESCRIPTION OF THE PREFERRED EMBODIMENTS

Figure 1:
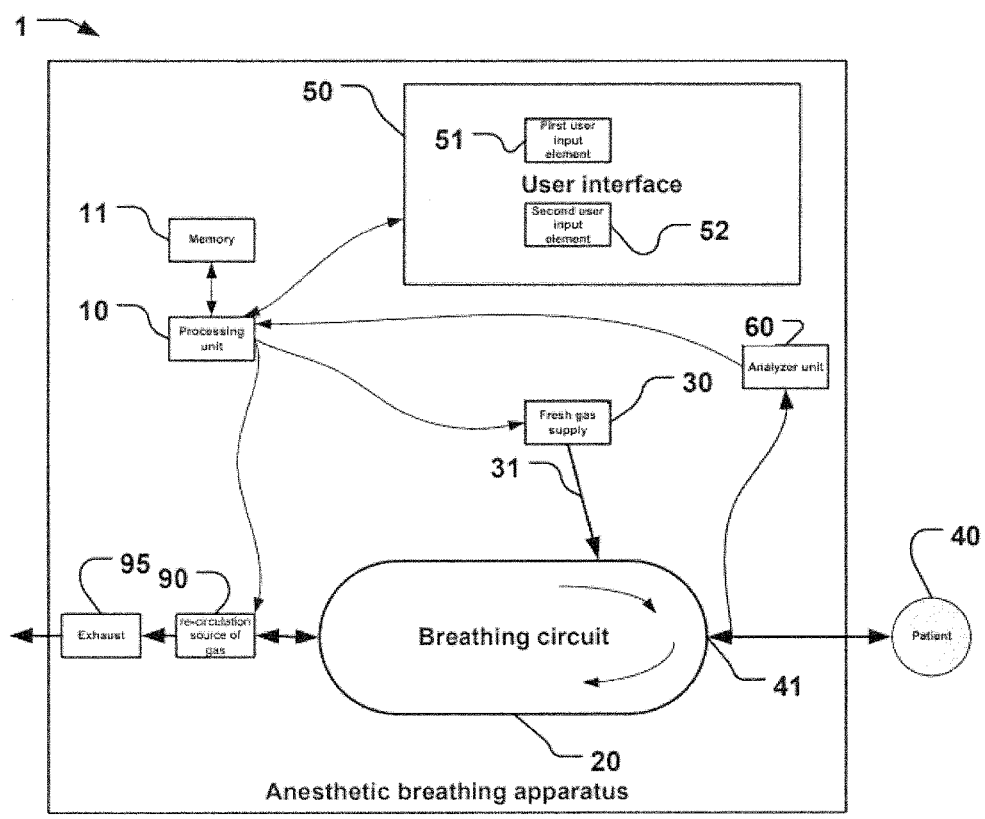
FIGS. 1 and 11 are schematic illustrations of anesthetic breathing apparatuses implementing examples of the present disclosure.

Specific examples of the disclosure will now be described with reference to the accompanying drawings. This invention may, however, be embodied in many different forms and should not be construed as limited to the examples set forth herein; rather, these examples are provided so that this disclosure will be thorough and complete, and will fully convey the scope of the invention to those skilled in the art. The terminology used in the detailed description of the examples illustrated in the accompanying drawings is not intended to be limiting of the invention. In the drawings, like numbers refer to like elements.

Automatic patient gas control is an operational mode in an anesthetic breathing apparatus where a flow and composition of fresh gas to a patient circuit is automatically controlled by a processing unit of the apparatus in order to achieve selected target values for FiO2 and an EtAA target concentration at the patient connection. Measured values, usually at the Y-piece by mainstream or side stream measurements are provided in a feedback loop for this control process.

All the examples of the disclosure pertain to and are operated in such automatic patient gas control operational mode in an anesthetic breathing apparatus.

Figure 2:
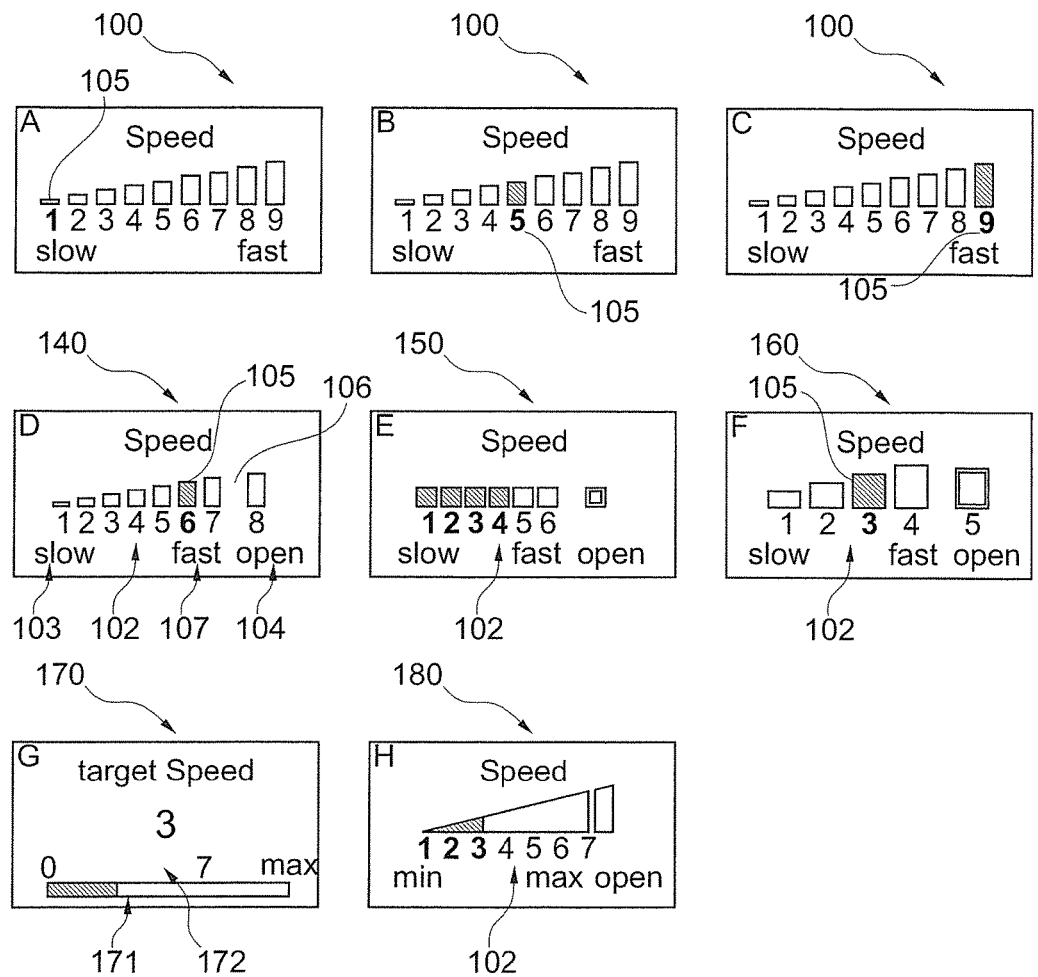
FIGS. 2A-H are graphical illustrations of examples for different control path selections.

When the automatic patient gas control operational mode is activated, the operator of the anesthetic breathing apparatus can adjust and select an anesthetic target value, such as a target EtAA value, for a desired level of anesthesia. The operator can in the example select a control profile 100, e.g. how quickly, the apparatus shall reach the target. The operator adjusts or selects the control path to the target EtAA by means of adjusting or selecting the exemplary parameter EtAA SPEED. The EtAA SPEED parameter may be selected from a range of values 102. Multiple discrete values may for instance be presented from a minimum 103 of the range 102 to a maximum 104 of the range 102. With reference to FIGS. 2A-C, an illustrative example is given with nine discrete steps. The nine discrete steps are merely an example. In FIGS. 2D-H some alternatives with a different number of steps displayed for selection, or even no discrete steps displayed at all. In case such an illustration is provided on a touch screen of the apparatus, the operator may use any one of the (exemplary) nine steps as a value for the control path, here the parameter EtAA SPEED, to reach the target value, here the EtAA target value.

In the example of the control profile 100, step 1 is associated with the slowest value of the range 102, while step 9 is associated with the fastest value of the range 102. The maximum rate 104 of change may be obtained in an open system, where fresh gas is directly supplied as patient gas without any re-breathed gas mixture. In the fastest mode, the desired anesthetic target value is obtained as quickly as possible. From the fastest mode to the slowest mode, a re-breathed gas portion is always present and the percentage thereof is the more increased, the slower the change is desired, e.g. in discrete steps.

FIG. 2D is an illustration of another example of a selector for a control profile 140, similar to that of FIGS. 2A-C. The EtAA SPEED parameter, i.e. the desired control profile, may be selected from a range of values 102. In this example, only 8 discrete values are presented from a minimum 103 of the range 102 to a maximum 104 of the range 102. A gap 106 is provided to illustrate an intermediate maximum value 107 of a sub-range. The maximum value is her, as in the aforementioned example an "open system". The value 107 correspond to the quickest of the "slower" steps explained above. Value 107 may be selected for a relatively quick change while still being economical, i.e. less waste gas. The gap 106 provides for the user to identify this boundary.

FIG. 2E provides another example of a selector for a control profile 150 with 7 steps. A gap is included between the fastest control profile, here for an open system, and the value "6" of the maximum of the sub range as explained above.

The selected value for the control profile may be visualized as a bar graph like that shown in FIG. 2E. The values up to the selected current control profile value are displayed in color different form a color of higher (not selected) values.

The bars may be increasing to illustrate the correspondingly higher value in the range 102 for easy identification by the operator.

A text may be provided at the selector or integrated there with, like in the examples "0", "slow", "min", "fast", "max", "open" etc. to assist the operator with clinical decisions and selections of desired control profiles. A text may be provided to identify the selector by the operator, like the text in the examples "Speed" or "target Speed". Other identification of the selector for a control profile in a user interface may include other texts like "Speed to target", and/or a symbol, or the like (not shown).

FIG. 2F provides another example of a selector for a control profile 160 with 5 steps, similar to the example of FIG. 2D.

FIG. 2G provides another example of a selector for a control profile 170 with no steps, but a continuous bar graph 171 and a metric value 172 or the selected control profile. The bar provides the user with the available range of values and where in the range the current value corresponding to a control profile is located within the range.

FIG. 2H provides another example of a continuous selector for a control profile 180 with no discrete steps. A bar with increasing height and a gap assist the operator in the user interface as described above.

Various other combinations of discrete bars, bar graphs, metrics, texts etc. than those illustrated in the Figs., as well as alternatives to these examples, can be envisaged by the skilled person when reading the present disclosure.

Figure 3:
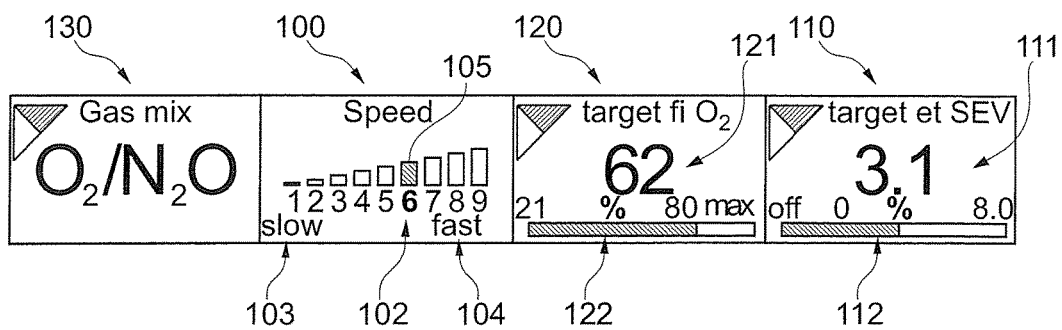
FIG. 3 is a graphical illustration of an example of selected control path and anesthetic targets for breathing parameters during automatic patient gas control.

The desired control profile is operator input and may have a default value prior to input. The currently active or selected value 105 for the desired control profile may be presented in a graphical way. An example is shown in FIGS. 2A-C and 3. In FIG. 3, the value is "6". This value may be a somewhat quicker control profile than an average control profile leading to a time to target somewhat quicker than average. In FIG. 2A, the slowest value "1" is provided. FIG. 2B, the "5" is provided, which might be an average time based on a corresponding target control profile. In FIG. 2A, the quickest value "9" is provided as the currently active or selected value 105.

In an example of the disclosure according to FIG. 1 an anesthetic breathing apparatus 1 is provided including a processing unit 10. FIG. 1 is a schematic illustrations of anesthetic breathing apparatuses 1 implementing examples of the present disclosure. Apparatus 1 includes a breathing circuit 20 for providing an inspiratory patient gas mixture of re-breathed gas and/or fresh gas to a patient 40 fluidly connected to the breathing circuit 20. The patient gas mixture is provided to the patient via a Y-piece 41. A fresh gas supply 30 is controllable by the processing unit 10 for supplying a flow of the fresh gas 31 via a conduit to the breathing circuit 20. The fresh gas is provided from a gas source (not shown) and one or more anesthetic agent vaporizing units (not shown) known in the art. The fresh gas is provided in a composition including at least oxygen to replace CO2 which has been in a CO2 absorber (not shown) removed from breathing gas expired by the patient 40. Fresh gas may include in a portion contain at least one anesthetic agent (AA) provided from the vaporizing unit(s). Fresh gas flow (volume per time) is controllable by the processing unit 10. The processing unit is also connected to a re-circulation source of gas 90, which during expiration receives expired gas from the patient 40 via the Y-piece 41 and the breathing circuit 20 as illustrated by the clockwise arrow leading from Y-piece 41 in FIG. 1. The re-circulation source of gas 90 may include a bag-in-bottle type bellows membrane, a reflector unit, or the like elements known for the skilled person allowing for providing re-breathed gas to the patient 40, e.g. for minimal (fresh gas) flow anesthesia. It is also connected to an exhaust 95 from the anesthetic breathing apparatus preferably connected to an EVAC system to handle exhaust waste gas from the apparatus 1. By controlling the fresh gas supply 30 and the re-circulation source of gas 90, a fraction of re-breathed gas supplied to the patient 40 during subsequent inspiration is controllable by processing unit 10.

Moreover, the apparatus has a user interface 50. The user interface 50 may be a conventional know based interface for user input. The user interface 50 may also in addition or alternatively include a touch sensitive display unit 55, such as a touch screen. The user interface includes a first user input element 51 for receiving operator input for an anesthetic target value including an end expiratory concentration of the AA (EtAA) target value and/or an end expiratory minimum alveolar concentration (MAC) target value of an end expiratory MAC value of the patient 40. Further, an oxygen target value may be received via the user interface 50 for an inspiratory oxygen portion in the inspiratory patient gas (FiO2). In international patent publication number WO2009/062540 of the same applicant as the present disclosure, control of MAC levels in anesthetic breathing apparatuses is disclosed. WO2009/062540 is incorporated herein by reference for all purposes.

The user interface 50 includes also a second user input element 52 for receiving operator input for a desired control profile for the fresh gas supply for obtaining at least the anesthetic target value. The processing unit 10 is configured to control the inspiratory patient gas mixture based on at least the anesthetic target value and the desired control profile. The oxygen target value or measured FiO2 value may be taken into consideration by the control process executed by the processing unit 10.

The control profile may have various shapes. It might be a linear ramp from a current value to the target value. The control profile may also have more complex shapes, like an exponential or other non-linear path from the current value to the target value. It should also be noted that the obtained control profile is based on continuous input from measurements related to the controlled parameter target. That means the obtained control profile when the target is reached may differ from the initially chosen control profile as it was updated during the control process. Deviations from initial control profiles may be caused by changes in patient uptake or metabolism, leakages, and other unforeseen events.

In a specific example, the anesthetic breathing apparatus 1 includes a display unit 55, and the processing unit 10 is operatively connected to the display unit 55. The display unit is preferably touch sensitive for operator input. The processing unit 10 is configured to provide on the display unit 55 a graphical user interface including at least one of a graphical visualization like shown in FIGS. 2 to 7.

The graphical user interface includes in an example a first user input element for receiving operator input, such as input on the touch sensitive display unit, for an anesthetic target value 110. The anesthetic target value may be input as an end expiratory concentration of the AA (EtAA) target value and/or an end expiratory minimum alveolar concentration (MAC) target value of an end expiratory MAC value of the patient. In the example illustrated in FIG. 3, a target value for Sevoflurane (SEV) is provided. The illustrated value is 3.1% SEV selected from a range 0 (OFF) to exemplary maximum 8.0%. This range and the currently selected target value are displayed as a metric 111. Alternatively, or in addition, a bar graph 112 may provide for displaying the current anesthetic target value 110 within a range of selectable values. The target value is operator input and may have a default value prior to input.

Input of a value may be made in conventional ways known to the skilled person, such as via physical or virtual knobs, numeric keyboards, sliders, selection for adjustment by tapping, confirmation steps, etc.

An oxygen target value for an inspiratory oxygen portion in the inspiratory patient gas (FiO2) 120 may be provided in the graphical user interface. A metric 121 and/or bar graph 122 may be provided for the FiO2 target value. The target value is operator input and may have a default value prior to input.

The graphical visualization includes also a second user input element for receiving operator input on the touch sensitive display unit for a desired control profile 100 for the fresh gas supply 30 for obtaining at least the anesthetic target value 110.

A selected fresh gas mix 130 may be displayed in addition.

Figure 4:
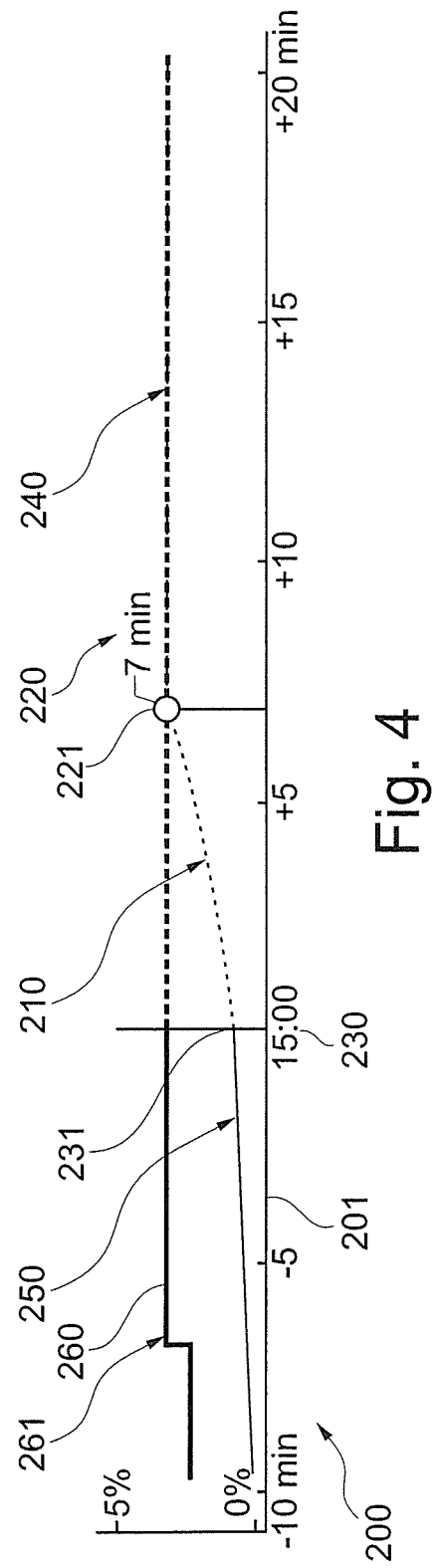
FIG. 4 is a graphical illustration of an example of a graph for visualization of an estimated progress of an anesthetic breathing parameter following a selected control path and showing an estimated time to achieve a selected target for that parameter.

Moreover, the graphical user interface may include a current time and/or an estimated duration or end time when at least one of the targets is reached and preferably an estimated path to reach the at least one target such as in a trend preferably including visualization of values of the EtAA and/or FiO2 measured before the current time and including a preview of the estimated path from the current time during the duration or until the end time. FIG. 4 is a graphical illustration of an example of a graph 200 for visualization of an estimated progress of an anesthetic breathing parameter following a selected control path 210 and showing an estimated time 220 to achieve a selected target 221 for that parameter. At the current time 230 along time axis 201, the anesthetic breathing parameter has an initial current value 231 from which the control process starts towards the target value 221. Once the target is reached, the value of the anesthetic breathing parameter levels out in portion 240 where the target value is maintained. Historical values of the anesthetic parameter are displayed as a trend section 250. The target value is shown as a curve 260. At point 261, the target value has been changed by the operator to a higher value. The estimation is elucidated in more detail below.

Figure 5:
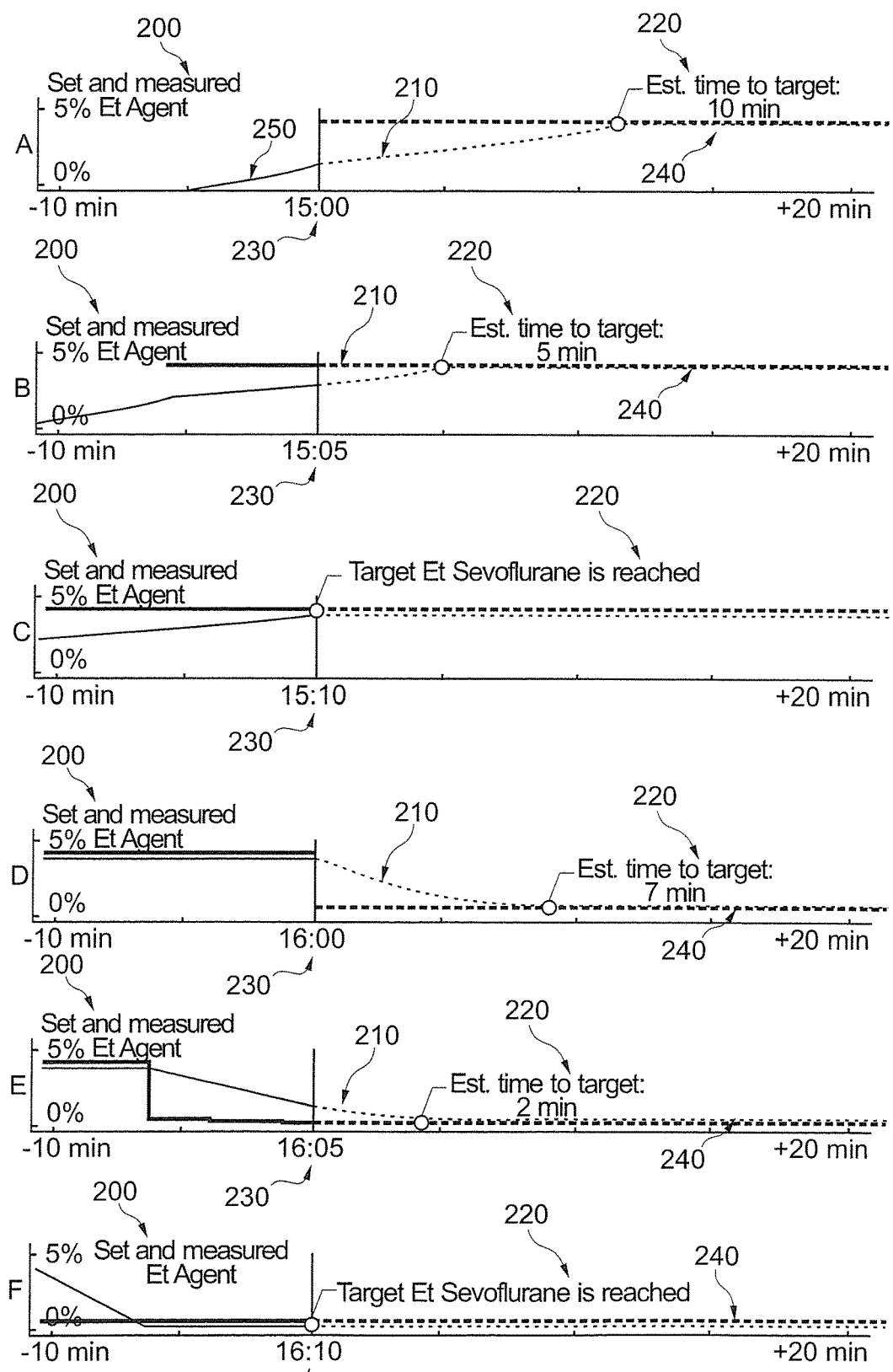
FIGS. 5 A-F, 6A-C, and 7A-D are graphical illustrations similar to FIG. 4 in various operational settings.

FIGS. 5 A-F, 6A-D, and 7A-C are graphical illustrations similar to FIG. 4 in various operational settings.

Ventilatory breathing parameters are not shown and ventilatory breathing modes during this automatic operational mode are not further discussed herein. It should be noted that the examples of present disclosure operate independent of such ventilatory breathing modes, like volume control, pressure control, etc.

FIGS. 5 A-F are provided to illustrate an example of a typical anesthesia session which is mostly run in an automatic operational mode for delivery of inhalational anesthesia to the patient by means of an apparatus 1.

In the example, the patient 40 is at the time of FIG. 5A at the beginning of anesthesia and shall be brought to a desired level of anesthesia. Current time in the example is 15:00. Inhalational anesthesia started approx. 5 minutes earlier in a conventional manner, e.g. by intravenous anesthesia induction, intubation, and ramping up of AA. At 15.00 the operator selects an anesthetic target value, here approx. 4% of an exemplary EtAA. The user also selects a desired control path to reach the target value. The processing unit 10 calculates the estimated time to target to be 10 minutes. The already ramped up AA is taken into consideration for the calculation. Such calculation is described in detail below. The estimated time to target and estimated control path to target is displayed, such as shown in FIG. 5A and the apparatus 1 is run in the automatic operational mode.

In FIG. 5B, approx. 5 minutes have lapsed. Current time in the example is 15:05. The processing unit 10 calculates the estimated remaining time to target to be 5 minutes. The trend portion of the graph shows the increase of AA towards the target EtAA.

In FIG. 5C, approx. further 5 minutes have lapsed. Current time in the example is 15:10 and 10 minutes have gone since activating the automatic operational mode. The EtAA target is reached, here as an example for Sevoflurane, illustrated in a message provided to the operator. The automatic operational mode is now continued maintaining this level of anesthesia. A surgical procedure may now for instance be performed, depending on the clinical operator's decision e.g. based on a required depth of anesthesia, patient condition, and other clinical parameters and requirements.

In FIG. 5D, approx. further 50 minutes have lapsed. Current time in the example is 16:00. The surgical procedure can be considered concluded and anesthesia shall be finished. The operator sets the EtAA target to 0%. A desired control path is selected by the operator and the estimated time to the new target is calculated and displayed, namely 7 minutes in the example.

In FIG. 5E, approx. further 5 minutes have lapsed. Current time in the example is 16.05. The EtAA level has decreased to approx. 1% and the estimated remaining time to target is 2 minutes.

In FIG. 5F, approx. further 5 minutes have lapsed. Current time in the example is 16.10. 10 minutes have lapsed since wash-out was initiated and the EtAA target is reached. Anesthesia can be concluded in a conventional way including extubating the patient and wake-up post anesthesia treatment.

Figure 6:
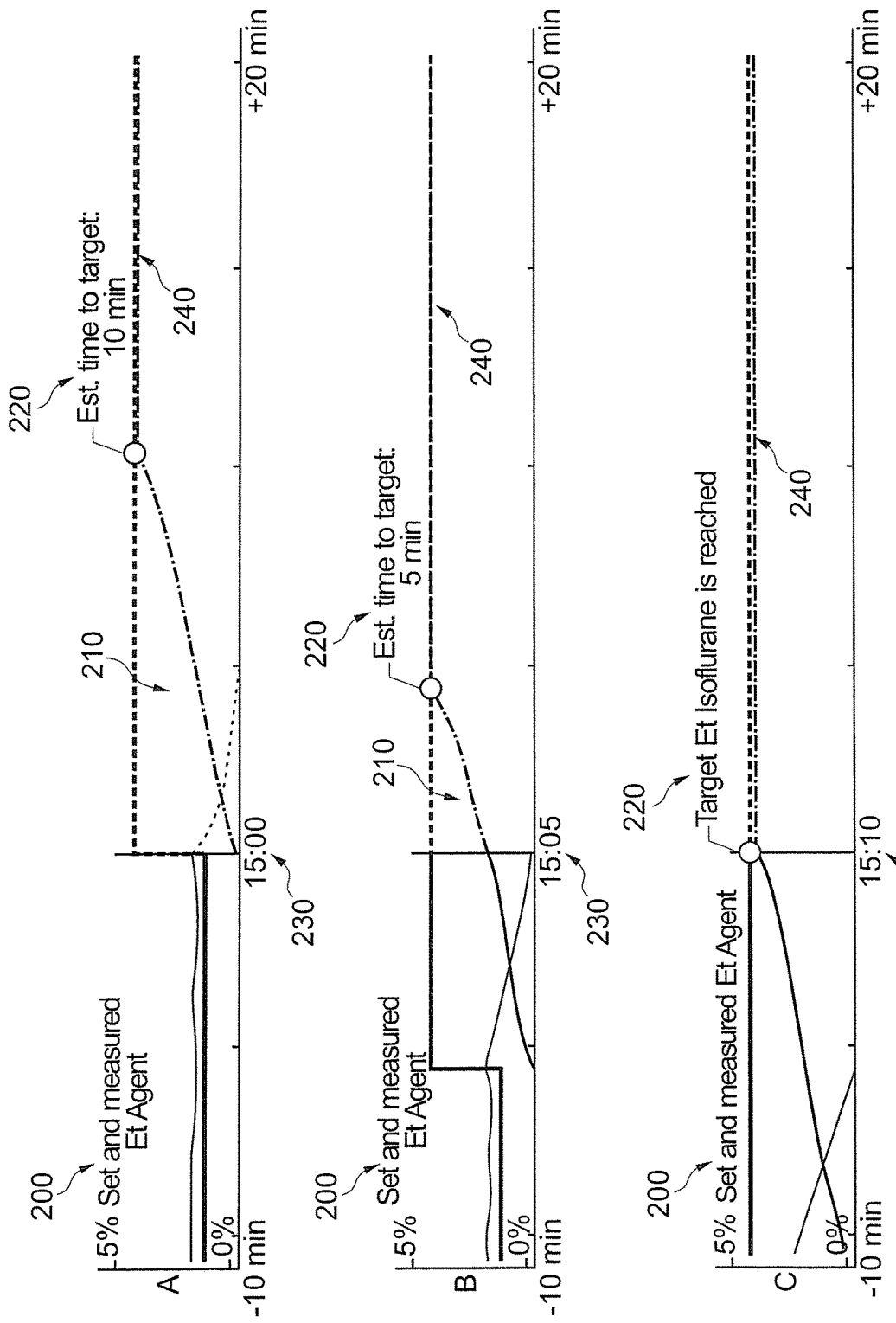

FIGS. 6 A-C are provided to illustrate an example when a first AA is changed to a second AA while maintaining a desired EtMAC target value. The apparatus 1 is run in an automatic operational mode for delivery of inhalational anesthesia to the patient 40.

In FIG. 6A, delivery has been switched from a first AA to a second AA, such as from Sevoflurane to Desflurane. Current time in the example is 15:00. The operator has selected the EtMAC target value to be constant despite the change of AA. The first AA will be ramped down to 0% while the second AA will be ramped up, here from 0%. A mixed MAC needs to be calculated by processing unit 10, which calculation is described in detail below.

In FIG. 6B, 5 minutes have lapsed. Current time in the example is 15:05. In the trend, the ramping up and down of the first and second AA can be seen.

In FIG. 6C, another 5 minutes have lapsed. Current time in the example is 15:10. The first AA is now completely washed out and the second AA has reached a level which corresponds to the EtMAC target. Note that the second AA has now a higher concentration than the first AA when changing AA. The transition process from the first AA to the second AA is non-linear and controlled by the processing unit 10.

Figure 7:
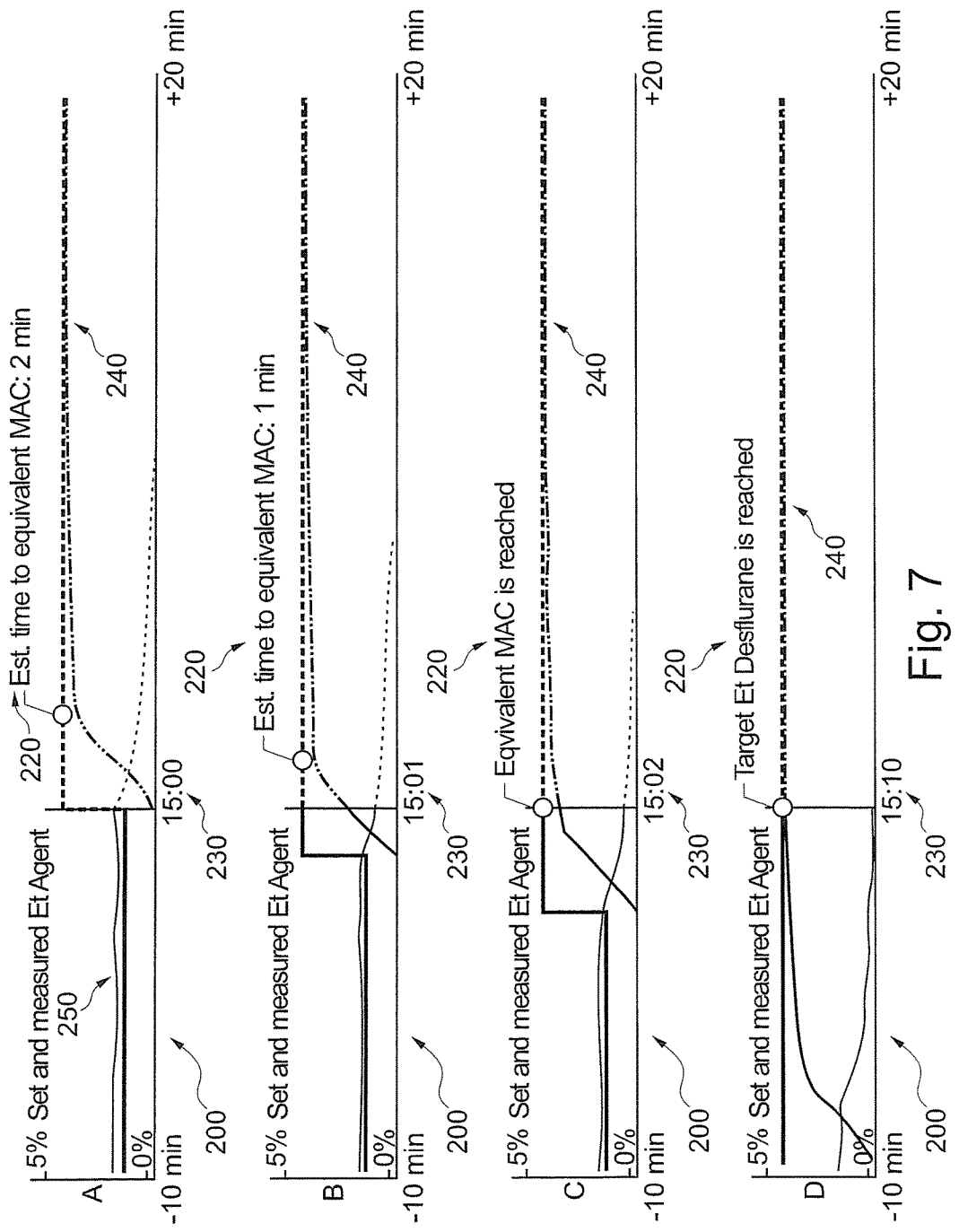

FIGS. 7 A-D are provided to illustrate an example when a first AA is changed to a second AA while a desired EtMAC target value is changed at the same time. The apparatus 1 is run in an automatic operational mode for delivery of inhalational anesthesia to the patient 40.

In FIG. 7A, delivery has been switched from a first AA to a second AA, such as from Sevoflurane to Desflurane. Current time in the example is 15:00. The operator has also selected an increased EtMAC target value. In addition, the operator has selected a specific control profile for the change of EtMAC to the EtMAC target value. The first AA will be ramped down to 0% while the second AA will be ramped up, here from 0%. A mixed MAC is calculated by processing unit 10 as long as both AA are present in expired patient gas mixture. In addition, processing unit 10 calculates an estimated time to the increased EtMAC value, in the example 2 minutes. An estimated control path for both the first and second AA are calculated and displayed.

In FIG. 7B, 1 minute has lapsed. Current time in the example is 15:01. Both the first and second AA are present as illustrated in the trend showing measured values. Estimated time to EtMAC target is a remaining 1 minute.

In FIG. 7C, another minute has lapsed. Current time in the example is 15:02. The target EtMAC is reached. Both the first and second AA are still present in the expired patient gas mixture. The target EtMAC is a mixed MAC value of the first and second AA.

Figure 10:
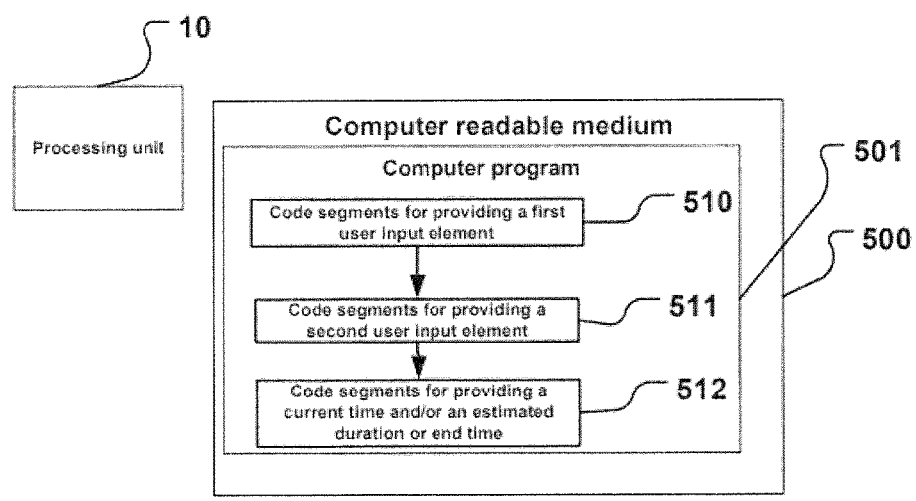
FIG. 10 is a schematic illustration of a computer readable medium having a computer program stored thereon for execution by a processing unit of an anesthetic breathing apparatus.

In FIG. 7D, 10 minutes have lapsed in total since switching AA. Current time in the example is 15:10. The target EtMAC has been maintained. The first AA is now washed out and has a value of 0%. The second AA has reached a target value maintaining the EtMAC target by a single AA, namely the second AA.

Figures 8, 9:
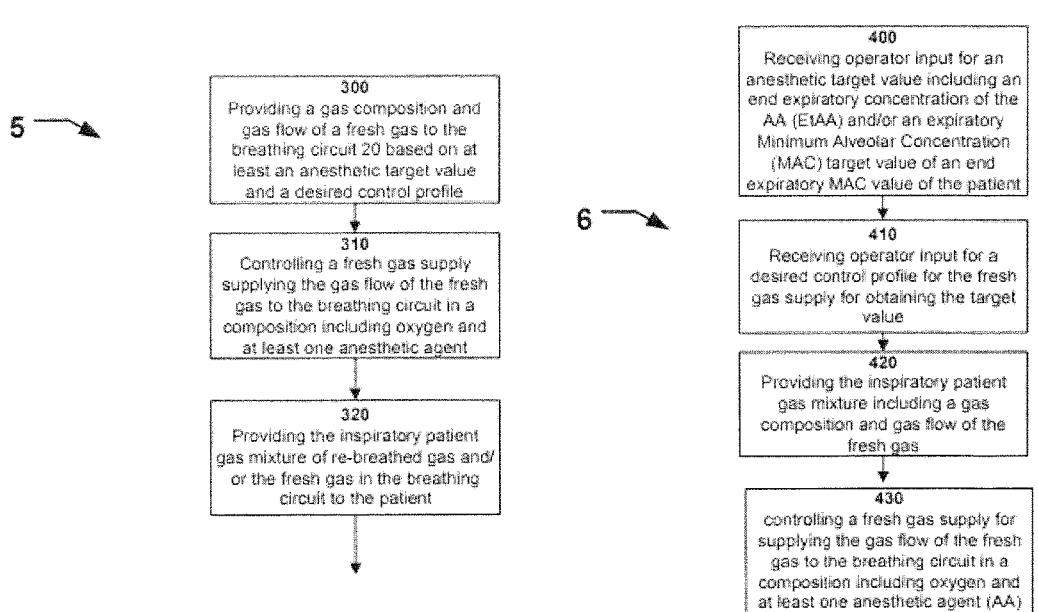
FIG. 8 is a flow chart illustrating an example of a control process of the present disclosure.
FIG. 9 is a flow chart illustrating an example of a method of the present disclosure.

FIG. 8 is a flow chart illustrating an example of a control process of the present disclosure. An internal control process 5 in an anesthetic breathing apparatus 1 is provided for controlling delivery of an inspiratory patient gas mixture from a breathing circuit 20 of the apparatus 1 to a patient 40 fluidly connected to the breathing circuit 20. The controlling of the inspiratory patient gas mixture includes providing 300 a gas composition and gas flow of a fresh gas to the breathing circuit 20 based on at least an anesthetic target value and a desired control profile, by controlling 310 a fresh gas supply supplying the gas flow of the fresh gas to the breathing circuit in a composition including oxygen and at least one anesthetic agent (AA). The oxygen target value or measured FiO2 value may be taken into consideration by the control process. The controlling 310 further includes providing 320 the inspiratory patient gas mixture of re-breathed gas and/or the fresh gas in the breathing circuit to the patient. The anesthetic target value is provided by operator input of an end expiratory concentration of the AA (EtAA) target value and/or an expiratory Minimum Alveolar Concentration (MAC) target value of an end expiratory MAC value of the patient and the desired control profile for the fresh gas supply is operator input for obtaining at least the anesthetic target value. Operator input may be provided for an oxygen target value for an inspiratory oxygen portion in the inspiratory patient gas (FiO2).

FIG. 9 is a flow chart illustrating an example of a method of the present disclosure. A method 6 is provided for controlling delivery of an inspiratory patient gas mixture of re-breathed and/or fresh gas from a breathing circuit 20 of an anesthetic breathing apparatus 1 to a patient 40 fluidly connected to the breathing circuit. The method 6 includes receiving 400 operator input for an anesthetic target value including an end expiratory concentration of the AA (EtAA) and/or an expiratory Minimum Alveolar Concentration (MAC) target value of an end expiratory MAC value of the patient. The method may include receiving operator input for an oxygen target value for an inspiratory oxygen portion in the inspiratory patient gas (FiO2). The method includes further receiving operator input 410 for a desired control profile for the fresh gas supply for obtaining the target value. Moreover, the method includes providing 420 the inspiratory patient gas mixture including a gas composition and gas flow of the fresh gas, by at least controlling 430 a fresh gas supply for supplying the gas flow of the fresh gas to the breathing circuit in a composition including oxygen and at least one anesthetic agent (AA), the controlling 430 being based on at least the anesthetic target value and the desired control profile for obtaining at least the anesthetic target value. The oxygen target value or measured FiO2 value may be taken into consideration by the control process implemented in the method 6.

The goal to be achieved by the EtAA control is to achieve or maintain the operator selected EtAA target for the selected type of agent, like Sevoflurane, Isoflurane or Desflurane. A Nitrous Oxide MAC component in patient gas does not influence the fresh gas EtAA control process. A Nitrous Oxide MAC component may however be considered for an operator selected MAC target, which is elucidated below.

In case one or more further anesthetic agents, different from the first anesthetic agent, can be found in expired patient gas, e.g. by a mainstream or side stream multi-gas analyzer unit 60 measuring at Y-piece 41, the MAC contribution of this or these further anesthetic agent(s) is taken into account by the control process for a target AA value executed by processing unit 10. This situation may for instance be present when a change from a first to a second AA is made and supports AA change without MAC level variation, thus maintaining a desired depth of anesthesia of the patient 40.

EtAA Control Process

The operator can not only adjust an anesthetic target value, but also the desired control path towards reaching the anesthetic target value. This is advantageous of many aspects, as described above. In a particular example, the operator can select a rate of change for the EtAA towards the selected anesthetic target value.

In the example, the control path is selectable in the form of pre-defined ramps that are presented to the operator as selectable rates of change (EtAA SPEED parameter). The ramps may be linear. It may be advantageous to provide non-linear ramps in some clinical context, e.g. with a higher rate of change at the beginning of the control process, which then transfers into a lower rate of change eventually flattening out when the anesthetic target is close or achieved. As there is provided updating feedback to the control process towards achieving the operator selected target in the desired control path, it should be noted that the selected control path will in practice be a guideline for the control process and deviations may occur, e.g. due to changes in metabolic rate etc. The ramp may have a positive or negative general slope, depending if the target value is higher or lower than the current value of the related parameter.

When a control path is selected for reducing to a lower anesthetic target value than a current value, the control process executed by the processing unit 10 takes into consideration that the patient washout of AA absorbed in the patient 40 prolongs the time in contrast to a ramp-up to a higher value. Absorbed AA needs to be washed out via the blood stream and then breath to breath via the lungs, i.e. the patient exhalation contributes with an amount of AA (re-) introduced into the breathing circuit. This reduces on the one hand the minimum time at which an EtAA target can be reached. On the other hand, this is taken into consideration by the control process. The control process may thus operate at suitable fresh gas and re-breathing settings to obtain a reduction to a lower anesthetic target value in a desired time. Maximum reduction to a zero target value may be obtained by providing a patient gas mixture of only fresh gas with no re-breathed gas. The fresh gas is then provided without any AA and at the minute volume of the patient ventilation. A time to reach the target will be based, amongst others, on the amount of AA absorbed in the patient 40, how large amount of AA needs to be washed out to reach the anesthetic target value, as well as transfer time of absorbed AA to be washed out of the patient. Any anesthetic target values may thus be provided with a selected control profile in an estimated time to target. The control process is operated at a suitable patient gas mixture including a suitable fresh gas flow and composition. The control process is continuously updated with measured data, including EtAA values.

The time to target can be regarded a transfer time or transition time of the control process to reach the target value.

In the example, a plurality of selectable "ramps" is illustrated. Each of the selectable change of rate for the control path is associated with a pre-defined ramp of selected shape and/or slope.

For each of the selectable change of rate, a pre-defined characteristic for the rate of change may be stored in a memory 11.

In a specific example, the slope of the ramp is different for each of the rates of change provided to the operator for selection, from slower (speed 1) to quicker (speed 9).

The fastest selectable time of change to reach a selected anesthetic target value, e.g. as the highest selectable rate of change (here speed 9), is when the inspired patient gas mixture is entirely composed of fresh gas delivered to the breathing circuit from the fresh gas supply 30. In this mode the fresh gas flow is set to the patient minute volume such that sufficient patient gas is provided to the patient from the fresh gas supply 30. Sufficient oxygenation of the patient is primarily ensured and e.g. monitored by hypoxia watch guards know in the art. The AA concentration delivered to the patient at this maximum rate of change may then be selected by the control process to be as high as possible with regard to patient safety and delivery capability of the apparatus as well as other parameters like maximum saturation in the fresh gas, etc., as the skilled person will be aware of.

Each selectable control profile may for instance be based on a desired time to target for reaching an increase from zero to one MAC. This provides for a desired control path of the profile, e.g. a linear path with a specific slope. The same slope may be used for the selected specific control profile, even if other targets or changes are to be controlled, such as 0.5 to 1 MAC. When reducing a MAC value, the slope is correspondingly negative, e.g. from 1 to 0 MAC in a desired time to target.

An example is for instance the following set-up for a change from 0-1 MAC, such as in the example illustrated in FIGS. 2A-C:

Speed 1: 30 min
Speed 2: 25 min
Speed 3: 20 min

Speed 4: 15 min
Speed 5: 10 min
Speed 6: 7 min
Speed 7: 4 min
Speed 8: 2 min
Speed 9: As Soon As Possible Estimation of Time and/or Path to Target Estimate In an example, the processing unit 10 is configured to calculate a time estimate until at least one of the target values is reached. The processing unit is preferably configured to update the time estimate continuously until the at least one target value is reached.

The estimate depends on a number of parameters on which the progress of the control process along a control profile depends. The development of the EtAA parameter having a selected target value will for instance depend on the current EtAA level when a (new) target is selected and activated by the operator. It will further depend on the patient's absorption profile. It also depends on the selected control profile. The estimation calculated by the processing unit 10 how the control process will proceed takes at least the aforementioned parameters into consideration for the estimation depending on the reliability of the estimated value desired. For a clinical operation it may be sufficient with a less than scientific approach regarding precision of the estimation. Also, the estimation is continuously updated during the control process based on actual outcome and measured values of for instance the EtAA parameter available to the processing unit 10.

In an example, the time estimate is updated based on measured EtAA values when the inspiratory patient gas mixture is being controlled by the processing unit based on at least the anesthetic target value and the desired control profile. The oxygen target value or measured FiO2 value may be taken into consideration for the time estimation.

The estimated time to target and/or estimated path to target may be provided upon selecting a specific control profile. The estimated time and/or path may be presented to the operator before confirming the selected control profile, i.e. accepting the selected control profile for continued operation of the apparatus 1. This provides for a clinical decision system facilitating the operator of the apparatus 1 to take suitable clinical decisions, e.g. depending on the patient's health condition and suitability for certain AA ramping times without risking adverse health effects such as blood pressure drop. The estimated time and/or path may then also be provided during the operation once it is accepted by the operator.

A graphical visualization may be presented on a display of the apparatus 1. The graphical visualization includes for instance a current time and the estimated duration or an end time when at least one of the targets is reached. An estimated path to reach the at least one target can be displayed, such as in form of a curve in a graph. Examples of such visualizations are given in FIGS. 4-7. The graph may include a curve of the target value of the selected control parameter.

The graph can present the history of the selected control parameter, such as the anesthetic target value as for instance the EtAA target value in a portion of the graph. The graph thus may include a trend portion that preferably includes visualization of values of the EtAA and/or FiO2 measured before the current time.

In another portion, the graph may include an estimated path for the development of the control parameter within the near future. The graph may thus include a preview of the estimated path from the current time during the duration or until the end time. The preview is in the examples shown as a dashed line of the control parameter towards its target value.

Once the target value is reached, the curve levels out.

A default value of target value and control profile may be stored in a memory of the breathing apparatus 1.

Calculation of EtAA Estimation

There are various ways to determine the estimation of time to target and/or path to target. Also, visualization of a time to target and/or path to target may be done in various ways. Some examples are described below.

One example of calculating the estimation of a time to target and/or path to target is to run a simulation of the control process based on current values, including current measured values of e.g. EtAA, the selected control target value, and the control profile for the control process. Calculation may be done iterative for the estimation of the control progress to target, i.e. for instance an increase in EtAA is feed back into the calculation as a new current value. Calculation of an increased EtAA value can be based on simulated increased AA concentration and/or fresh gas flow contributing to increase inspired AA in the patient gas mixture. In this manner, a plurality of resulting calculation values for a specific time from calculation start, for e.g. EtAA values, resulting from the control path are obtained, which calculation values and their time stamp can be stored in a memory in operative communication with the processing unit 10. Once the control target value is obtained, that time includes the time to target and the path to the target. These values may then be suitably presented to the operator, such as in the examples herein.

During induction, i.e. beginning of anesthesia, the start value for EtAA will be zero. If the calculation starts with a value or EtAA different from zero, the development up to this value may be considered in the calculation of the estimated time to target and/or path to target. Analysis of the development to EtAA increase and/or decrease the current EtAA value result in control parameters like uptake of AA in the patient, metabolic uptake of the patient, etc.

An initial estimation may for instance be based on a pre-defined control path, e.g. for a ramp to target, which the control process follows. This kind of initial estimation works very reliable when the patient physiology does not limit the control process. For instance when reducing to a lower target EtAA, the wash-out from the patient usually has a slower time constant than the anesthetic breathing apparatus.

An initial estimation may for instance be based on an amount of AA which is estimated that the patient has absorbed, as well as known patient characteristics and known mathematical models for absorption in a patient and wash-out of AA from a patient.

An initial estimation may for instance be based on an amount of AA which is estimated that the patient has absorbed, as well as an estimation of a time constant for the patient based on measured EtAA values in relation to AA dosage given and the time of that dosage.

This initial estimation may then be updated continuously during operation of the control process. As measured valued, e.g. of EtAA, are available, the initial prediction may deviate from the current control path result. Upon such deviations, the estimated control path is re-calculated.

A specific example for such re-calculation is that the processing unit 10 for the control process combines the initial estimation with measured EtAA by creating a buffer memory with a first in first out (FIFO) principle. The FIFO buffer memory is used continuously to calculate the estimated path to target. The FIFO buffer memory is updated for each measured EtAA value, i.e. after each breath as follows:

When the operator adjusts a target value, the processing unit 10 creates a virtual history of in the FIFO buffer memory for calculated values of the initial estimated path to target.

When new EtAA values are measured and available to the processing unit 10, these values are stored in the FIFO buffer memory.

In case the control process fails to influence the patient's EtAA value as expected by the estimated path to target of the control process, the new values in the FIFO buffer memory will cause the estimation calculation to adapt to this fact. This means that the estimation of the control path to the target value, such as the EtAA target value, will create an improved estimation with each breath, which estimation better corresponds to the real control process obtained.

When the control process can keep up with the selected control profile, the FIFO buffer memory is filled with values that correspond to a similar control path in the buffer. The estimated path to target is then not changed substantially.

When the control process cannot keep up with the selected control profile, for instance when AA is washed out of the patient, the FIFO buffer memory is filled with values that provide for an improved estimation of the control path to target.

In order to provide a desired update rate and precision, the size of the FIFO buffer memory can have varied size. The size can be dynamically optimized. For instance, the FIFO buffer memory is initially provided in a first pre-defined memory size. The memory size may be increased when the control process cannot keep up with the selected control profile. In this manner, a quicker correction of an estimation calculation may be provided. In addition, or alternatively, the initial memory size may be increased to a larger memory size as measurement values are collected. The more values in the FIFO buffer memory, the better the adaptation to the control path obtained. The initial memory size may be reduced in case the EtAA development is discontinuous, e.g. when an O2 flush is performed, a large leakage is present in the system, etc.

The operator may be presented with a plurality of pre-defined control paths, from which to select one specific control path for operation of the apparatus 1. The operator may in other examples define a desired control path. The operator may enter a desired duration to reach a desired target value, as well as a control path to reach the target of the control profile. The operator may enter a desired curve to be followed as a control path towards the target. The curve may be entered via a suitable user interface, such as graphically, e.g. via a touch sensitive display unit. In this manner, the operator may even more specifically enter the best suited path to target for specific clinical needs.

EtMAC Control

As an alternative to control the patient's 40 depth of anesthesia by means of controlling EtAA to a desired target value, the control process may be based on a target EtMAC and EtMAC control profile. A difference between EtAA target control and EtMAC control is that the EtMAC control process also takes the MAC contribution of Nitrous Oxide, when used, into consideration.

The objective for a MAC based control is to achieve and/or maintain a selected MAC value for a combination of one or more selected AA(s) (Isoflurane, Sevoflurane, Desflurane etc.) and Nitrous Oxide (N2O). If the FiO2 value is changed, the available portion in the patient gas mixture for AA and N2O is changed too. Hence, the target value for AA and N2O is changed correspondingly in the control process if the FiO2 value is changed, while the target EtMAC value remains unchanged.

In case more than one AA is measured end tidally, the contribution of these one or more secondary AA to the total MAC value in addition to the primary AA is taken into consideration by the control process. As the control process maintains a target EtMAC, a desired depth of anesthesia is maintained even when concentrations of AA(s) and/or N2O are varied. Such situation may occur when changing from a primary AA to a secondary AA. Calculation of such a "mixed MAC" of a plurality of contributing components (AAs, N2O) is known to the skilled person and for instance described in international patent publication number WO2009/062540 of the same applicant as the present disclosure, which is incorporated herein by reference for all purposes.

FIG. 10 is a schematic illustration of a computer readable medium 500 having a computer program 501 stored thereon. The computer program 501 is provided for processing by a processing unit 10 of the anesthetic breathing apparatus 1 for controlling delivery of an inspiratory patient gas mixture from a breathing circuit 20 of the apparatus 1. The apparatus 1 includes a display unit 55, and the processing unit 10 is operatively connected to the display unit 55. The processing unit 10 is further configured to provide on the display unit 55 a graphical visualization. The computer program 501 comprises code segments for providing the graphical visualization including code segments for providing a first user input element 510 for receiving operator input on the touch sensitive display unit for an anesthetic target value including an end expiratory concentration of the AA (EtAA) target value and/or an end expiratory minimum alveolar concentration (MAC) target value of an end expiratory MAC value of the patient. The computer program 501 may include a code segment for providing a user input element for an oxygen target value for an inspiratory oxygen portion in the inspiratory patient gas (FiO2). The computer program comprises code segments for providing a second user input element 511 for receiving operator input on the touch sensitive display unit for a desired control profile for the fresh gas supply for obtaining at least the anesthetic target value. The computer program comprises code segments for providing a current time and/or an estimated duration or end time when at least one of the targets is reached 512 and preferably an estimated path to reach the at least one target such as in a trend preferably including visualization of values of the EtAA and/or FiO2 measured before the current time and including a preview of the estimated path from the current time during the duration or until the end time.

Figure 11:
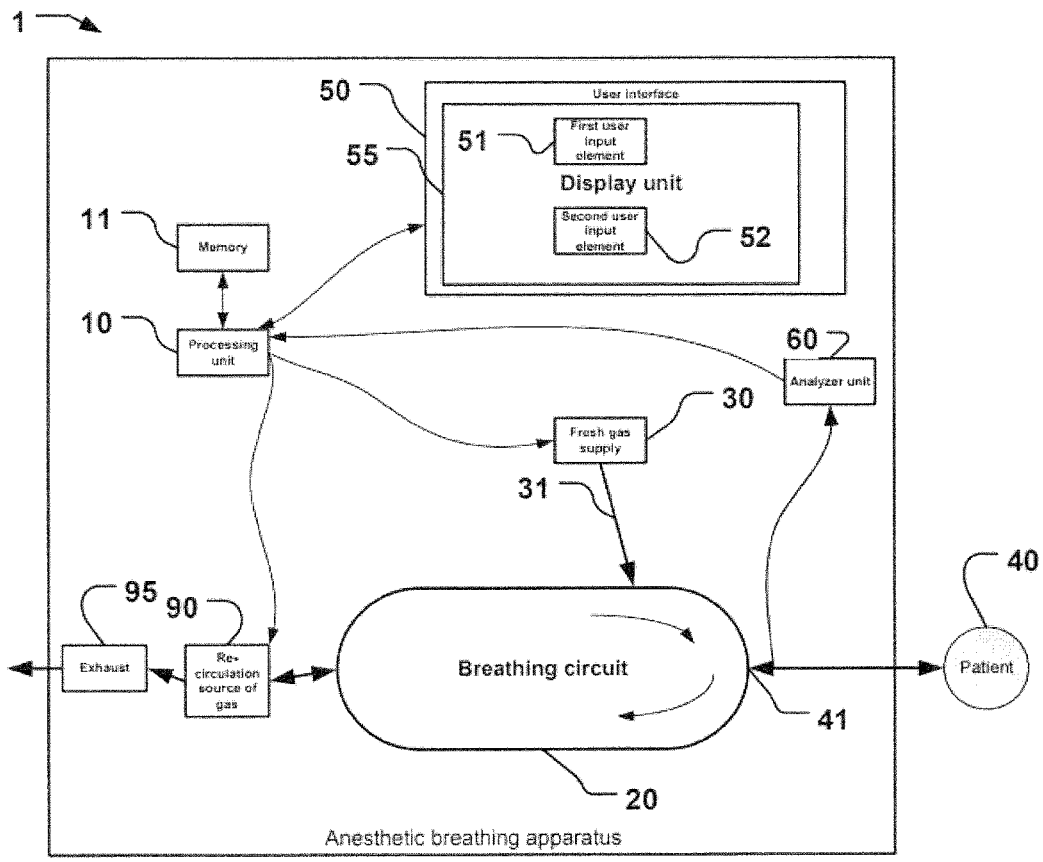
Figure 12:
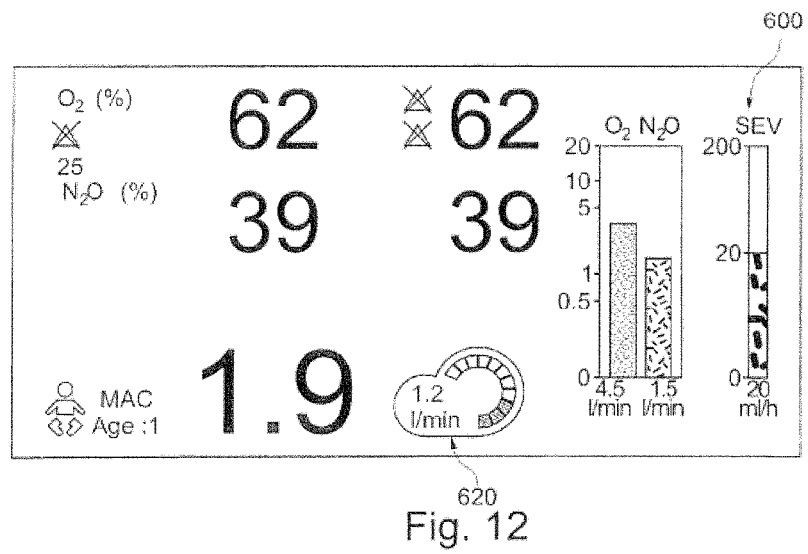
FIG. 12 is a graphical illustration of an example of a graphical visualization on a display of an anesthetic breathing apparatus during an automatic anesthesia delivery operational mode.
Figure 13A:
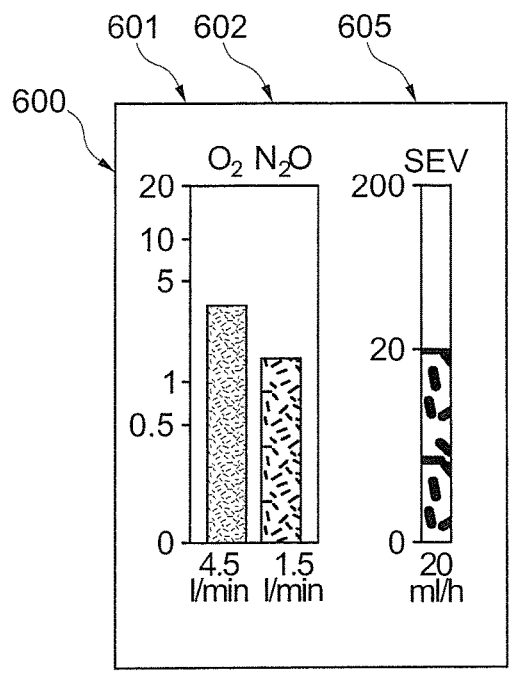
FIGS. 13A and 13B are graphical illustrations of an example of a graphical illustration for delivery of fresh gas, as shown in FIG. 12.
Figure 13B:
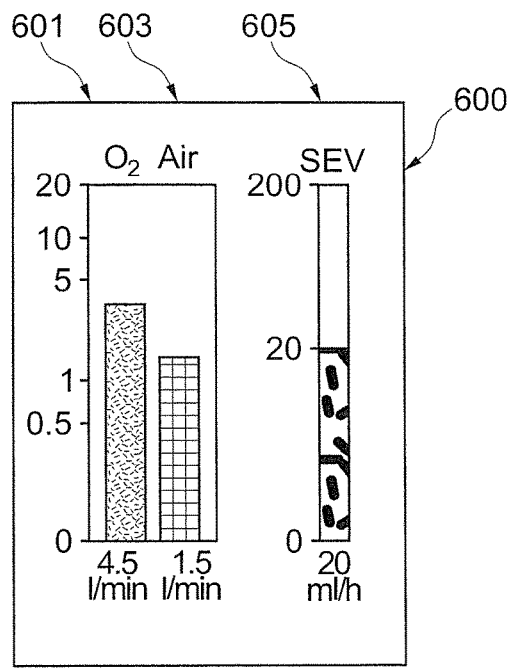

FIG. 11 is a schematic illustration of an anesthetic breathing apparatus 1 implementing examples of the present disclosure. The anesthetic breathing apparatus 1 is provided including a display unit 55 and a processing unit 10 being operatively connected to the display unit 55. The apparatus includes a breathing circuit 20 for providing an inspiratory patient gas mixture of re-breathed gas and/or fresh gas to a patient 40 fluidly connected to the breathing circuit. Further, the apparatus 1 includes a fresh gas supply 30 controllable by the processing unit 10 for supplying a flow of the fresh gas to the breathing circuit in a composition including at least oxygen and air or nitrous oxide, and at least one anesthetic agent (AA). The apparatus has an automatic operational mode for delivery of inhalational anesthesia to the patient. The processing unit 10 is configured to provide on the display unit 55 a graphical user interface (GUI) during the automatic operational mode. The GUI includes a first visualization unit 600 as shown in FIGS. 12, 13A and 13B. The first visualization includes a bar and metric for flow of a measured oxygen portion O2 601 in the composition of the fresh gas flow, a bar and metric for flow of a measured nitrous oxide portion N2O 602 in the composition of the fresh gas flow or a bar and metric for flow of a measured air portion 603 in the composition of the fresh gas flow, a bar and metric for flow of a measured portion of the AA in the composition of the fresh gas flow. The first visualization unit 600 of the GUI includes alternatively or in addition a second visualization unit 620, see FIGS. 12 and 15A-E. The second visualization includes a metric 621 for the total measured fresh gas flow updated for each breath supplied to the patient, and an animation portion 622 for visualizing a fresh gas flow to the breathing circuit. The animation 622 is moving during ongoing fresh gas delivery to the breathing circuit only.

There is a need for such a visualization of the function of an anesthetic breathing apparatus automatic anesthesia modes of the apparatus. As the apparatus automatically controls fresh gas and AA delivery in this operational mode, some operators have a desire to receive feedback on the operation of the apparatus. Some operators are conventionally used to make all adjustments and digest readings of measured values when operating an anesthetic breathing apparatus. However, in automatic anesthesia modes, the operator selects desired target values and the apparatus automatically calculates necessary patient breathing gas mixture delivery and operates the apparatus accordingly. The operator is no longer actively making these adjustments. Delivery is made during the entire time the automatic anesthesia mode is activated by the operator. Therefore, there exists a need for some operators to provide a feedback on the actual values of delivered fresh gas flow and composition including delivered AA despite the fact that the operator no longer actively makes adjustments of this delivery in the automatic anesthesia mode.

This need is met by visual indicator provided to the operator. The indicator provides to the operator a status of the apparatus, namely that fresh gas delivery control is performed for a fresh gas flow delivered at a certain composition.

The indicator has in an example a cloud like shape icon, as in the example of FIGS. 12, and 15A-E. Within the icon, an animation is provided visualizing ongoing fresh gas delivery during inspiration. At the end of inspiration of a breathing cycle, the total delivered fresh gas flow is displayed as a metric 621. The animation 622 provides the user with confidentiality that gas delivery is ongoing.

In addition, see FIGS. 12 and 13A,B, columns are displayed for each component of the fresh gas composition and the individual flow delivered with the total fresh gas flow displayed as the metric. The columns may comprise O2 and Air plus AA, or O2 and N2O plus AA, the values of which are updated for each breath. Units for O2, Air and N2O are liters per minute (l/min) and for AA milliliters per hour (ml/h). The display of the delivered AA allows for a calculation of remaining time until liquid AA has to be re-filled, depending on a size of the container for AA at the vaporizer for the AA. FIG. 12 is a graphical illustration of an example of a graphical visualization on a display of an anesthetic breathing apparatus during an automatic anesthesia delivery operational mode.

Figure 14:
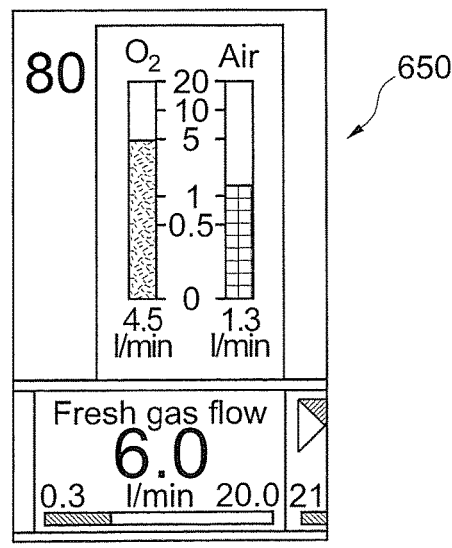
FIG. 14 is a graphical illustration of measured values of delivered breathing gas components.
Figure 15:
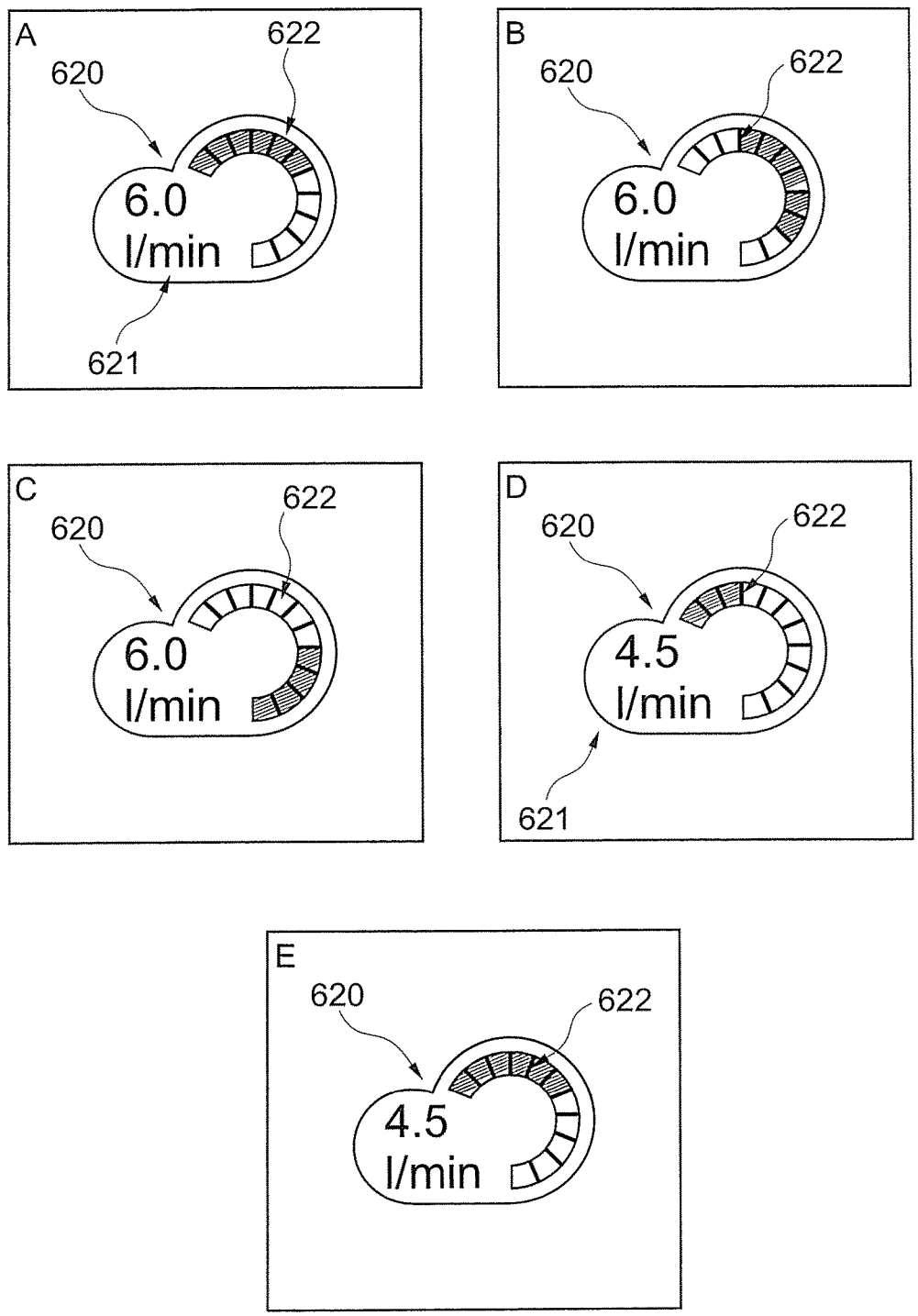
FIGS. 15A-E are graphical illustrations of total fresh gas flow and an indication of operation.

Measured values may have a specific background color, like black as in the enclosed FIGS. 12, 13A and 13B. When the apparatus is operated in non-automatic anesthesia modes, two of the columns may be displayed, namely for O2 and Air/N2O, wherein adjusted values are shown and not measured values. The background may have a different color to illustrate this different operational mode and difference in values, as e.g. a grey background shown in the exemplary FIG. 14. FIGS. 15A-E are graphical illustrations of measured values of delivered breathing gas components. FIG. 14 is a graphical illustration of a setting for fresh gas components and flow.

Some exemplary embodiments include the following:

16. An internal control process in an anesthetic breathing apparatus for controlling delivery of an inspiratory patient gas mixture from a breathing circuit of said apparatus to a patient fluidly connected to said breathing circuit, said controlling of said inspiratory patient gas mixture including providing a gas composition and gas flow of a fresh gas to said breathing circuit based on at least an anesthetic target value, and a desired control profile, by controlling a fresh gas supply supplying said gas flow of said fresh gas to said breathing circuit in a composition including oxygen and at least one anesthetic agent (AA), and further providing said inspiratory patient gas mixture of re-breathed gas and/or said fresh gas in said breathing circuit to said patient;

wherein said anesthetic target value is provided by operator input of an end expiratory concentration of said AA (EtAA) target value and/or a expiratory Minimum Alveolar Concentration (MAC) target value of an end expiratory MAC (EtMAC) value of said patient and said desired control profile for said fresh gas supply is operator input for obtaining at least said anesthetic target value.

17. A computer-readable medium having embodied thereon a computer program for processing by a processing unit of an anesthetic breathing apparatus for controlling delivery of an inspiratory patient gas mixture from a breathing circuit of said apparatus, said apparatus including a touch sensitive display unit, and said processing unit being operatively connected to said display unit, said processing unit further being configured to provide on said display unit a graphical visualization, the computer program comprising code segments for providing said graphical visualization including code segments for providing a first user input element for receiving operator input on said touch sensitive display unit for an anesthetic target value including an end expiratory concentration of said AA (EtAA) target value and/or an end expiratory minimum alveolar concentration (MAC) target value of an end expiratory MAC (EtMAC) value of said patient, a second user input element for receiving operator input on said touch sensitive display unit for a desired control profile for said fresh gas supply for obtaining at least said anesthetic target value; and a current time and/or an estimated duration or end time when at least one of said targets is reached and preferably an estimated path to reach said at least one target such as in a trend preferably including visualization of values of said EtAA and/or FiO2 measured before said current time and including a preview of said estimated path from said current time during said duration or until said end time.

18. A method of controlling delivery of an inspiratory patient gas mixture of re-breathed and/or fresh gas from a breathing circuit of an anesthetic breathing apparatus to a patient fluidly connected to said breathing circuit, wherein said method includes:

receiving operator input for an anesthetic target value including an end expiratory concentration of said AA (EtAA) and/or a expiratory Minimum Alveolar Concentration (MAC) target value of an end expiratory MAC (Et-MAC) value of said patient, receiving operator input for a desired control profile for said fresh gas supply for obtaining said anesthetic target value, providing said inspiratory patient gas mixture including a gas composition and gas flow of said fresh gas, by at least controlling a fresh gas supply for supplying said gas flow of said fresh gas to said breathing circuit in a composition including oxygen and at least one anesthetic agent (AA), said controlling being based on at least said anesthetic target value and said desired control profile for obtaining at least said anesthetic target value.

19. An anesthetic breathing apparatus including a display unit and a processing unit being operatively connected to said display unit, a breathing circuit for providing an inspiratory patient gas mixture of re-breathed gas and/or fresh gas to a patient fluidly connected to said breathing circuit, and a fresh gas supply controllable by said processing unit for supplying a flow of said fresh gas to said breathing circuit in a composition including at least oxygen and air or nitrous oxide, and at least one anesthetic agent (AA), said apparatus having an automatic operational mode for delivery of inhalational anesthesia to said patient, and said processing unit being configured to provide on said display unit a graphical user interface including during said automatic operational mode a graphical visualization including in combination:

a first visualization unit including a bar and metric for flow of a measured oxygen portion in said composition of said fresh gas flow, a bar and metric for flow of a measured nitrous oxide portion in said composition of said fresh gas flow or a bar and metric for flow of a measured air portion in said composition of said fresh gas flow, a bar and metric for flow of a measured portion of said AA in said composition of said fresh gas flow; and a second visualization unit including:

a metric for said total measured fresh gas flow, and an animation for visualizing a fresh gas flow to said breathing circuit, said animation moving during ongoing automatic operational mode only.

The present disclosure has been described above with reference to specific examples. However, other embodiments than the above described are equally possible within the scope of the invention. Different method steps than those described above, performing the method by hardware or software, may be provided within the scope of the invention. The different features and steps of the disclosure may be combined in other combinations than those described. The scope of the invention is only limited by the appended patent claims.

We claim as our invention:

1. An anesthetic breathing apparatus comprising a processing unit, a breathing circuit for providing an inspiratory patient gas mixture of re-breathed gas and/or fresh gas to a patient fluidly connected to said breathing circuit, and a fresh gas supply controllable by said processing unit for supplying a flow of said fresh gas to said breathing circuit in a composition including oxygen and at least one anesthetic agent (AA), and a user interface comprising:

a first user input element for receiving operator input for an anesthetic target value including an end expiratory concentration of said AA (EtAA) target value and/or an end expiratory minimum alveolar concentration (MAC) target value of an end expiratory MAC (Et-MAC) value of said patient, a second user input element for receiving operator input for a desired control profile for said fresh gas supply for obtaining said anesthetic target value, wherein the control profile includes an operator selected time to reach the anesthetic target value and/or an operator selected control path to reach said anesthetic target value from a current EtAA value or EtMAC value, and wherein said control profile includes a desired rate of change for obtaining at least one of said EtAA and/or said EtMAC value;

said processing unit being configured to control said inspiratory patient gas mixture based on said anesthetic target value and said desired control profile.

2. The apparatus of claim 1, wherein said processing unit is configured to control at least said fresh gas flow and composition from fresh gas supply for said control of said inspiratory patient gas mixture, such that said inspiratory patient gas mixture includes at least in a portion said fresh gas when supplied to said breathing circuit.

3. The apparatus of claim 1, wherein said control profile includes a rate of change for obtaining said anesthetic target value from a current level of said EtAA.

4. The apparatus of claim 3, wherein said rate of change is selectable from a range for said rate of change having a minimum value and a maximum value, wherein said second user input element in particular includes a plurality of operator selectable discrete steps ranging from said minimum value to said maximum value.

5. The apparatus of claim 4, wherein said processing unit for said maximum value is configured to control said fresh gas flow to be the only gas composition in said inspiratory patient gas mixture delivered to said patient, and wherein said processing unit for values in said range of said rate of change other than said maximum value is configured to control said fresh gas flow to be less than a flow of said inspiratory patient gas mixture delivered to said patient.

6. The apparatus of claim 5, wherein said processing unit is configured to provide a ramp function with a pre-defined pitch for each of said discrete steps between said current level of said EtAA and said anesthetic target value.

7. The apparatus of claim 1, wherein said processing unit is configured to calculate an updated time to target continuously until said at least one of said EtAA and/or said EtMAC value is reached.

8. The apparatus of claim 7, wherein said time estimate is updated based on measured EtAA values when said inspiratory patient gas mixture is being controlled by said processing unit based on said anesthetic target value and said desired control profile.

9. The apparatus of claim 1, wherein said at least one anesthetic agent (AA) includes at least a first AA and a second AA, and wherein said anesthetic target value is based on said second AA when switching from said first AA to said second AA, or said anesthetic target value is an EtMAC value based on both said first AA and said second AA.

10. The apparatus of claim 1, wherein said user interface includes a display unit operatively connected to said processing unit, and wherein said processing unit is configured to:

calculate an estimated duration or end time from a current time to when at least one of said EtAA and/or said EtMAC value is reached and to calculate an estimated path to reach said at least one of said EtAA and/or said EtMAC value, and communicate said duration or end time to said display for visualization, said visualization including a preview of said estimated path from said current time at least during said duration or until said end time.

11. The apparatus of claim 10, wherein said processing unit is configured to continuously calculate and update said estimated duration or end time and/or said estimated path to reach said at least one target, based on measured values of said EtAA and/or FiO2.

12. An anesthetic breathing apparatus comprising a touch sensitive display unit and a processing unit being operatively connected to said display unit, a breathing circuit for providing an inspiratory patient gas mixture of re-breathed gas and/or fresh gas to a patient fluidly connected to said breathing circuit, and a fresh gas supply controllable by said processing unit for supplying a flow of said fresh gas to said breathing circuit in a composition including oxygen and at least one anesthetic agent (AA), said processing unit being configured to provide on said display unit a graphical user interface including a graphical visualization comprising:

a first user input element for receiving operator input on said touch sensitive display unit for an anesthetic target value including an end expiratory concentration of said AA (EtAA) target value and/or an end expiratory minimum alveolar concentration (MAC) target value of an end expiratory MAC (EtMAC) value of said patient a second user input element for receiving operator input on said touch sensitive display unit for a desired control profile for said fresh gas supply for obtaining at least said anesthetic target value; wherein the control profile includes an operator selected time to reach the anesthetic target value and/or an operator selected control path to reach said anesthetic target value from a current EtAA value or EtMAC value, and wherein said control profile includes a desired rate of change for obtaining at least one of said EtAA and/or said EtMAC value; and a current time and an estimated duration or end time when at least one of said targets is reached.

* * * * *